US009008462B2

(12) United States Patent
Akhbardeh et al.

(10) Patent No.: US 9,008,462 B2
(45) Date of Patent: Apr. 14, 2015

(54) METHODS AND SYSTEMS FOR REGISTRATION OF RADIOLOGICAL IMAGES

(75) Inventors: Alireza Akhbardeh, Baltimore, MD (US); Michael A. Jacobs, Sparks, MD (US)

(73) Assignee: The Johns Hopkins University, Baltimore, MD (US)

( * ) Notice: Subject to any disclaimer, the term of this patent is extended or adjusted under 35 U.S.C. 154(b) by 20 days.

(21) Appl. No.: 14/000,003

(22) PCT Filed: Feb. 17, 2012

(86) PCT No.: PCT/US2012/025708
§ 371 (c)(1),
(2), (4) Date: Aug. 16, 2013

(87) PCT Pub. No.: WO2012/112929
PCT Pub. Date: Aug. 23, 2012

(65) Prior Publication Data
US 2013/0322723 A1 Dec. 5, 2013

Related U.S. Application Data

(60) Provisional application No. 61/443,770, filed on Feb. 17, 2011.

(51) Int. Cl.
*G06K 9/32* (2006.01)
*G06T 3/40* (2006.01)
*A61B 6/03* (2006.01)
*A61B 6/00* (2006.01)
(Continued)

(52) U.S. Cl.
CPC . *G06T 3/40* (2013.01); *A61B 6/032* (2013.01); *A61B 6/037* (2013.01); *A61B 6/5247* (2013.01);
(Continued)

(58) Field of Classification Search
USPC ......... 382/100, 128, 130, 131, 132, 154, 276, 382/278, 286, 289, 291, 293, 294, 295, 296, 382/297, 298, 299, 302; 378/4–27; 128/922; 345/548–671; 348/561, 581, 348/582, 583, 704; 358/451; 708/208
See application file for complete search history.

(56) References Cited

U.S. PATENT DOCUMENTS 4,998,286 A * 3/1991 Tsujiuchi et al. ............. 382/165
7,248,751 B2 * 7/2007 Schuler et al. ................ 382/284
(Continued)

FOREIGN PATENT DOCUMENTS

JP 2005087727 A 4/2005
JP 2006095267 A 4/2006

OTHER PUBLICATIONS

International Search Report and Written Opinion dated Aug. 22, 2012 issued in PCT/US2012/025708.

*Primary Examiner* — Anand Bhatnagar
(74) *Attorney, Agent, or Firm* — Mintz Levin Cohn Ferris Glovsky and Popeo, P.C.

(57) ABSTRACT

Featured are methods and systems for reslicing-based non-rigid registration of multiparametric and modality images or objects. In such registration methods, global motion is modeled by multiple affine transforms (rigid), while local motion and slices matching is estimated using non-uniform radial reslicing of RTV to search for best match between reference volume slices and resampled target volume (RTV), orthogonally re-sliced to higher spatial resolution compared to the spatial resolution of the reference volume. The reference and target volumes can be in any plane and the method presented in this invention transfers them to target plane which can be any of axial, coronal, or sagittal and there is no need for the original and target scanning planes to be the same.

18 Claims, 18 Drawing Sheets

(51) Int. Cl.
*A61B 8/13* (2006.01)
*A61B 8/08* (2006.01)
*G01R 33/56* (2006.01)
*G06T 7/00* (2006.01)
*G06T 3/00* (2006.01)

(52) U.S. Cl.
CPC ............... *A61B 8/13* (2013.01); *A61B 8/5246* (2013.01); *G01R 33/5608* (2013.01); *G06T 7/003* (2013.01); *G06T 3/0068* (2013.01); *A61B 6/5223* (2013.01); *A61B 6/5264* (2013.01); *G01R 33/5601* (2013.01); *G06T 2207/10072* (2013.01); *G06T 2207/20064* (2013.01); *Y10S 128/922* (2013.01)

(56) References Cited

U.S. PATENT DOCUMENTS

| | | | | |
|---|---|---|---|---|
| 7,623,700 | B2* | 11/2009 | Sogawa | 382/154 |
| 8,160,345 | B2* | 4/2012 | Pavlovskaia et al. | 382/131 |
| 8,406,527 | B2* | 3/2013 | Kido | 382/193 |
| 8,532,361 | B2* | 9/2013 | Pavlovskaia et al. | 382/131 |
| 2008/0095470 | A1* | 4/2008 | Chao et al. | 382/298 |
| 2008/0232712 | A1* | 9/2008 | Matsui et al. | 382/277 |
| 2008/0292164 | A1* | 11/2008 | Azar et al. | 382/131 |
| 2009/0226067 | A1* | 9/2009 | Souza et al. | 382/131 |

* cited by examiner

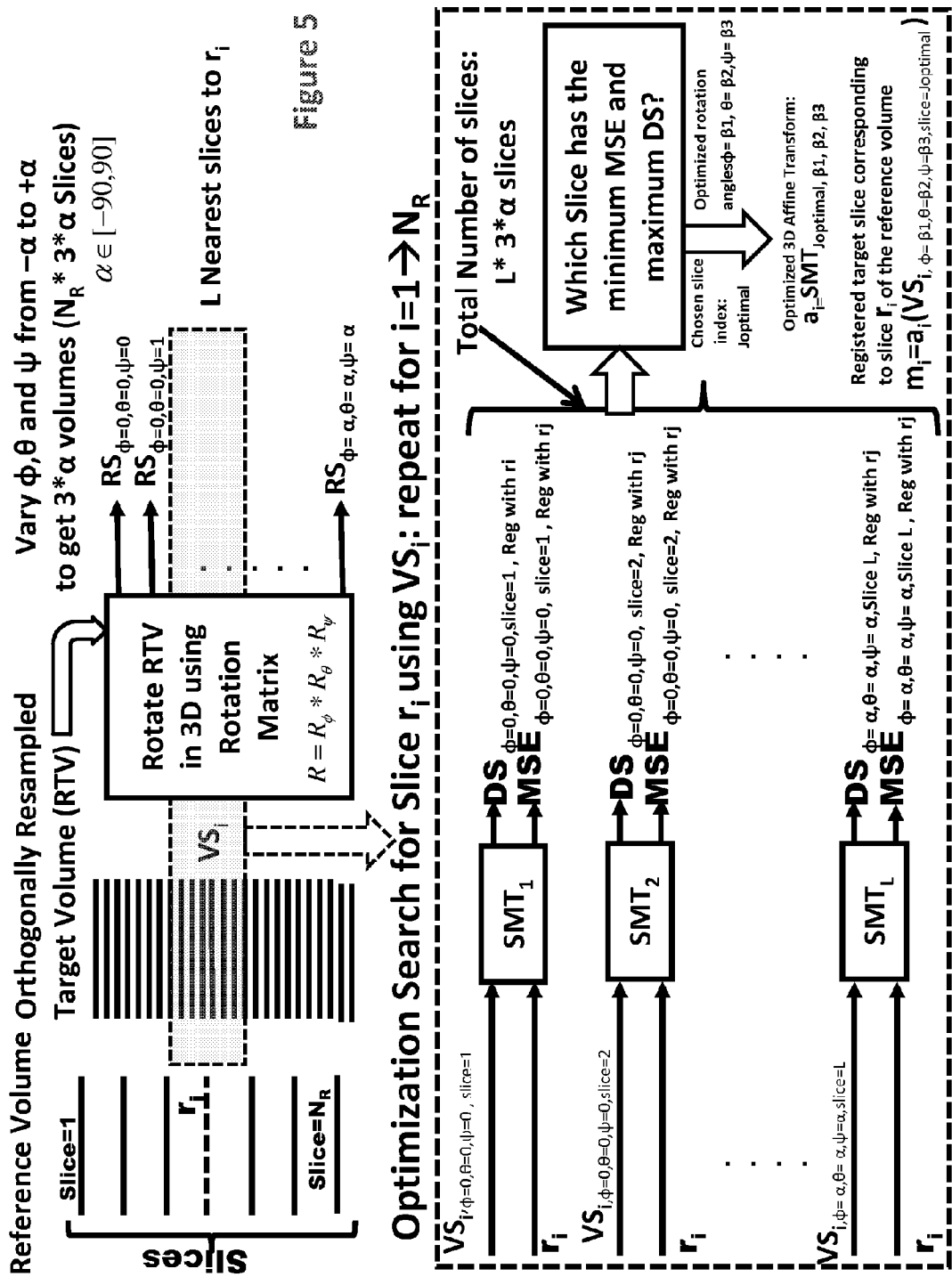

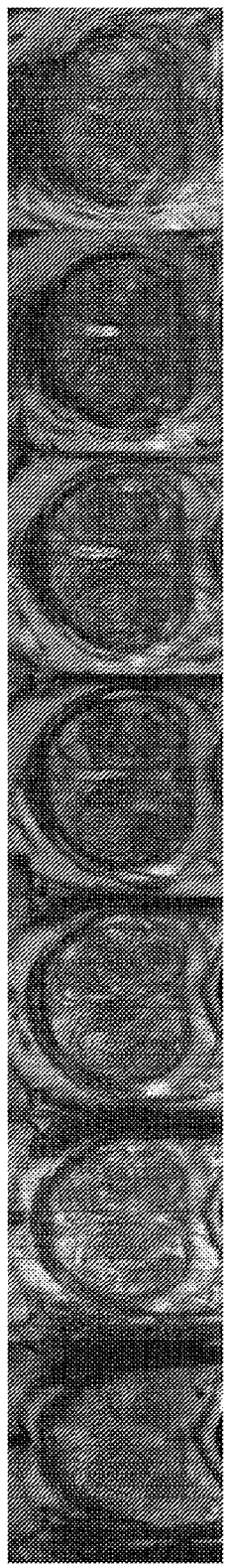
Figure 7

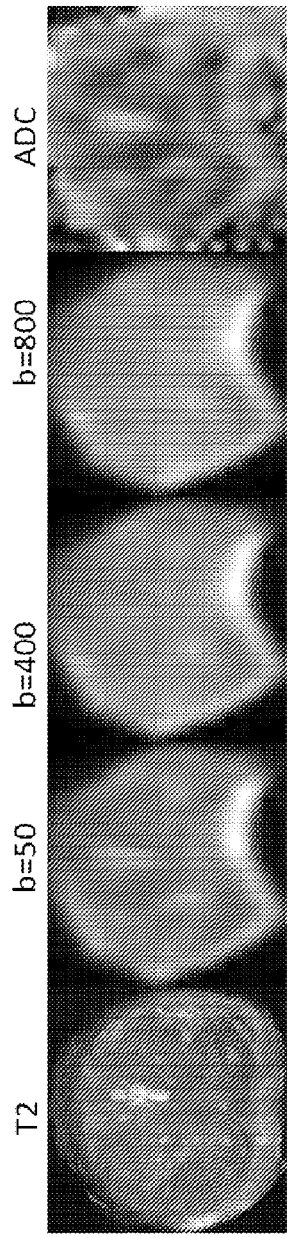 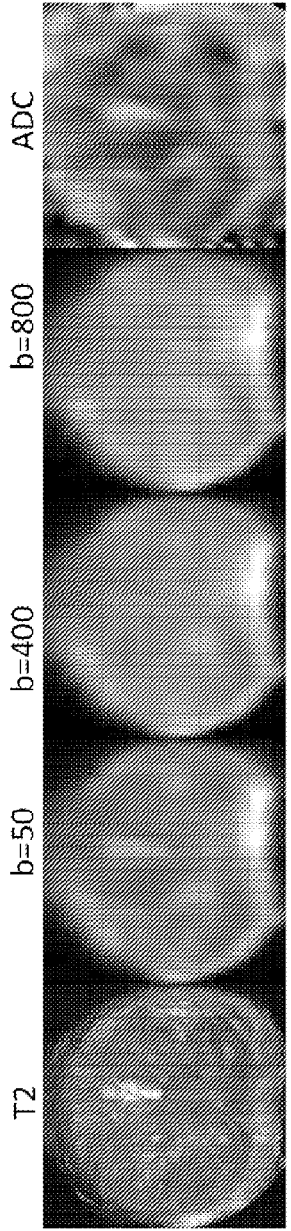
Scanning Plane=Axial, Number of Images= 15, Image Size= 320x320, Spatial Resolution=4.0x2.19x2.19mm³
MR parameters: T2-wesigned (T2), Diffusion-Weighted-Imaging (b=50,400,800), ADC Map.
Figure 8

METHODS AND SYSTEMS FOR REGISTRATION OF RADIOLOGICAL IMAGES

CROSS-REFERENCE TO RELATED APPLICATIONS

This application is a 35 U.S.C. §371 U.S. national stage entry of International Application PCT/US2012/025708 (WO 2012/112929) having an International filing date of Feb. 17, 2012, which claims the benefit of U.S. Provisional Application Ser. No.: 61/443,770, filed Feb. 17, 2011, which are incorporated herein by reference in their entirety.

FIELD OF INVENTION

The present invention generally relates to image reconstruction techniques, more particularly to 3D registration of multiparametric and modality images or objects.

BACKGROUND OF THE INVENTION

Image registration is the process of finding a transformation that aligns one image to another. Within the broad area of research, medical image registration has emerged as an active field and is becoming a valuable tool for various medical image processing applications [Lester and Arridge 1999; Periaswamy and Farid 2003; Rohlfing, Maurer et al. 2003; Cao and Ruan 2007; Zhang, Arola et al. 2010]. In other words, the importance of medical image registration is due in part to the many clinical applications including diagnosis and surgical planning, and to the need for registration across different imaging modalities such as MRI, X-RAY, UT, CT and PET.

Current image registration methods in use are either prospective or retrospective [Van Den Elsen, Pol E et al. 1993; Peitryz, Herholz et al. 1996]. Prospective registration techniques require external markers (fiducial markers) in place before the desired scan is obtained and during any subsequent scans and this methodology has proven to be logistically difficult in the clinical setting. In contrast, retrospective methods are attractive because they can be applied at any time after the acquisition of the image data and require no external devices. The retrospective techniques currently in use are surface matching [Pelizzari, Chen et al. 1987; Pelizzari, Chen et al. 1989; Jiang, Robb et al. 1992; Rusinek, Tsu et al. 1993; Turkington, Jaszczak et al. 1993], principal axes transformation [Gamboa-Aldeco, Fellingham et al. 1986; Alpert, Bradshaw et al. 1990; Toennies, Udupa et al. 1990; Holupka and Kooy 1992; Rusinek, Tsu et al. 1993], and voxel intensity matching [Wells, Viola et al. 1996; Woods, Grafton et al. 1998].

The image registration, similar to other problems in the image processing, is an optimization process to minimize a cost function that characterizes the similarity between the source and target images. Some algorithms use a complementary cost function (e.g., the regularization or penalty term to control particular deformations and constrain the transformation between the source and target images. In some registration algorithms this term is called the smoothness and biharmonic constraint penalty (or thin-plate model) term that is proportional to the deflection bending energy of a thin plate. Some other algorithm use a penalty term called the Laplacian or membrane model term that is proportional to the deflection energy of a membrane.

Current medical image registration, however, still presents many challenges. Several notable difficulties are 1) the transformation between images can vary widely and be highly nonlinear in nature; 2) the transformation between images acquired from different modalities may differ significantly in overall appearance and resolution; and 3) each imaging modality introduces its own unique challenges, making it difficult to develop a single generic registration algorithm. Some other notable difficulties include: 4) some imaging techniques such as echo planar image (EPI) data used in functional imaging, can exhibit severe localized geometric distortion; 5) nonrigid registration techniques, which are base on intensity, often produce transformations that substantially change the image (object) volume; and 6) histological comparison with in-vivo image data is complicated due to many factors in the image data such as pixel or voxel size, slice orientation, and/or the number of slices obtained. The most prominent factors affecting correlation with histological sections result from the histological fixation process that causes shrinkage, tearing, and distortion of the tissue.

Another challenging problem is with registration of radiological images acquired before and after therapy. This problem is more critical in registration of pre-contrast with post-contrast image pairs. Since tumors typically change shape and volume during treatment, the intensity-based registration algorithms may compress or expand tumors during the registration process and therefore provide results that are misleading in regard to tumor response. This miss-registration severely affects the use of the registered images in the post-processing such as image subtraction, volumetric analysis, multi-spectral classification, and pharmacokinetic modeling. This especially happens in the registration of high-resolution anatomical images with lower resolution pharmacokinetic parameters obtained from sequential Dynamic Contrast Enhanced MRI (DCE-MRI).

The above mentioned problem occurs because intensity-based registration algorithms are designed to minimize an intensity inconsistency between the two images. As the image intensity profile changes after therapy and injection of the contrast agent, a direct comparison of image intensities with sum of squared intensity differences or correlation cannot be used as an image similarity measure. In this case mutual information could be used as an alternative cost function that has been shown to accurately and robustly align images from the same patient that are acquired from different image modalities. However this solution is only an effective similarity measure for rigid registration and fails to preserve contrast-enhancing structures from substantially changing size in nonrigid registration. Hayton et al. used a modified optical flow algorithm with a constraint based on a pharmacokinetic model of the contrast uptake. The goodness of fit of the uptake model provides a consistency criterion for the registration.

A different approach specifically designed to address the problem of volume loss couples the control points of a free-form (B-spline) deformation in order to make the contrast-enhancing lesion locally rigid. Because the structures are enforced to be rigid, this approach prevents deformation of the structures even in cases where they have actually deformed. A novel physics-based regularization term to constrain the deformation has been developed by Rohlfing et al. Global motion is modeled by a rigid transformation while local motion is described by a free-form deformation based on B-splines. Registration is performed by searching for the deformation that minimizes a cost function consisting of a weighted combination of the image similarity measure (normalized mutual information) and a regularization term which is a local volume-preservation (incompressibility) constraint based on the concept that soft tissue is incompressible for small deformations and short time periods. That is, the tissue can be deformed locally, but like a gelatin-filled balloon, the volume (local and total) remains approximately constant. The incompressibility constraint is implemented by penalizing deviations of the Jacobian determinant of the deformation from unity. A constraint term proposed by Rohlfing et al. was combined with an extension of the adaptive bases algorithm (ABA) by Li et al. to control the compression or expansion of a tumor for registration of MR images before and after therapy. However, these regularization approaches are only designed for DCE-MR images to address the specific problem of volume loss in the nonrigid registration of contrast-enhanced images and are not suitable for multimodal image registration.

It thus would be desirable to provide new methods and systems for image registration, more specifically, reslicing-based nonrigid 3D registration of the radiological images.

SUMMARY OF THE INVENTION

According to one aspect of the present invention there are featured methods and systems for reslicing(resampling)-based nonrigid 3D registration of radiological images. Global motion is modeled by a 3D affine transform (rigid) while local motion and slices matching is estimated using non-uniform resampling of the pixel intensities of the target image volume along the reference plane. The reference plane is the plane that the reference image volume is scanned. The target plane can be any of axial, coronal, or sagittal and there is no need for the reference and target scanning planes to be the same.

In such methods and systems, registration is performed by searching for a resamples angles and reslicing planes that maximizes similarity between the reference image volume and the resliced target image volume. The estimated reslicing angles can be between −90 and 90 degree. By angular (radial) reslicing of the target image volume, the number of slices of the reference and target volumes will be the same and it deforms the target volume to morph it with the reference image volume. Such a reslicing-based nonrigid registration of the radiological images according to this aspect of the present invention is a useful tool to match slices location and thickness, and 3D registration of the image or object slices.

Such methods and systems are particularly suitable for, for example: 3D reslicing of different modalities to match field of view (FOV); 3D reslicing of different modalities to match slice locations; 3D reslicing of different modalities to match slice thickness; 3D reslicing of different modalities to match image sizes; 3D reslicing different modalities using Wavelet transform and interpolation; 3D reslicing to correct displacement, rotation, and tilt of modalities; 3D slice by slice angular or radial reslicing to deform or warp and maximize similarity between the target and reference image; 3D reslicing of different modalities to transfer image data to the desired plane (e.g., Sagittal, Coronal, and/or axial) and 3D registration to preserve global and local volume. Such methods and systems of the present invention also are suitable for application to in-vivo to ex-vivo registration of different modalities.

In yet further aspects of the present invention, there is featured a method for registration of multiparametric and modality images or objects. Such a method comprises acquiring image data in slices and processing the acquired image data. Such processing comprises three steps: (1) resizing number of slices in one of a plurality of planes or all planes to a desired size using orthogonal reslicing and to obtain resampled target volume (RTV), (2) registration parameters estimation based on non-uniform radial reslicing: searching for best match between reference slices and resampled target volume (RTV) slices, and (3) non-uniform radial reslicing comprising (i) 3D rotation, (ii) slice-by-slice affine transformation (translation and scale only) of the resampled target volume (RTV), and (iii) search which slices of RTV, after applying (i) and (ii), are similar and/or very similar to slices of the reference volume.

In regards to the references herein and in the claims as to slices of RTV being similar or very similar to the reference volume, a reference volume slice and/or to slices of the reference volume, as described herein, a least square based method named Similarity Maximized Transform (SMT) is used to find which one of M slices and with which translation and scale is very similar to a reference slice $r_1$. This is done by looking at mean-square-error (MSE) and dice similarity (DS) between reference and target images, dice similarity (DS) is defined Dice similarity index is calculated:

$$DS = 2\frac{A \cap B}{A + B}$$

where A and B are respectively binary makes extracted from $r_1$ and a slice of RS volume. Between M slices driven from 3D iterative rotations of RTV, a slice of RTV with index $j_{optimized}$ that provides the highest DS and lowest MSE is chosen as the best match with reference slice $r_1$. The resultant is the image $g_1 = a(RTV(j_{optimized}))$, which has the highest similarity index and minimum mean-square-error with $r_1$. a(.) is the estimated 3D affine transform with parameters $\phi_1$, $\theta_1$ and $\psi_1$, $h_1$ and $s_1$.

In embodiments of the present invention, the 3D rotation angles is defined by the relationship ($\phi$, $\theta$ and $\psi$), where $\phi$, $\theta$ and $\psi$ can be between −90 and 90 degree. Also, the reslicing plane is one of axial, coronal and/or sagittal.

In yet further embodiments, such non-uniform radial resampling includes 3D affine transforms ($A=\{a_i\}_{i=1:NR}$) to select some of slices of resampled target volume (RTV), obtained by 3D resampling of the target volume to a spatial resolution higher than spatial resolution of the reference volume, in a non-uniform manner such a 3D affine transform includes parameters of 3D rotations, translation and scaling estimated using an optimization search routine, such as explained herein (see FIG. 5).

In yet further embodiments, such processing of the acquired data includes correcting for at least one of field of view, slice thickness and orientation.

In yet further embodiments, the imaging technique is one of a MRI, CT, X-ray, PET and UT imaging technique.

In yet further embodiments such acquiring image data includes acquiring image data of a given region of interest using one imaging technique and acquiring image data for said given region of interest using a second imaging technique and wherein said processing includes processing the acquired image data from both imaging techniques so that the image data of said one technique is co-registered with the acquired data using said second imaging technique. Where one imaging technique is one of a MRI, CT, X-ray, PET and UT imaging technique and wherein said second imaging technique is the other of an MRI, CT, X-ray, PET and UT imaging technique.

In yet further embodiments, such acquiring image data includes acquiring one image data of a given region of interest using one imaging technique and acquiring another image data for said given region of interest using said one imaging technique; wherein said processing includes processing the acquired image data for said one and said another imaging data, and wherein said imaging technique is one of a MRI, CT, X-ray, PET and UT imaging technique.

In yet further aspects/embodiments of the present invention there is featured, a method for 3D registration of multiparametric and modality images or objects. Such a method includes acquiring image data in slices and processing the acquired image data. Such processing comprises three steps: 1) orthogonal reslicing (resampling): resampling number of slices and image matrix size of target image volume to a desired size (Number of slices=$N_D$, image matrix size=$R_D \times C_D$) using orthogonal reslicing, name new target volume as resampled target volume (RTV). $N_D$, $R_D$ and $C_D$ are at least two times bigger than number of slices=$N_R$, image matrix size=$R_R \times C_R$ for the reference volume; 2) Non-Uniform Radial Reslicing: start with the first slice of the reference volume ($r_1$), choose L nearest slices of RTV, name it as $VS_1$ and search for 3D rotation angles ($\phi$, $\theta$ and $\psi$), translation (h) and scale (s) that makes one of slices of $VS_1$, with slice index $j_{optimal}$ in original volume RTV, similar to or very similar to $r_1$. L is resolution increase rate and equals to number of slices of RTV divvied by number of slices of the reference volume. The resultant is the image $g_i = a(RTV(j_{optimal}))$, which has the highest similarity index and minimum mean-square-error with $r_1$. a(.) is the optimized 3D affine transform with parameters $\phi = \beta_1$, $\theta = \beta_2$ and $\psi = \beta_2$, $h = h_1$ and $s = s_1$; 3) To register with all slices of the reference volume, repeat the search routine (step 2) $N_R$ times to get image volume of $G = \{g_i\}_{i=1:NR}$, which is the registered volume with the reference volume R using optimized 3D affine transforms $A = \{a_i\}_{i=1:NR}$. $N_R$ is number of slices for the reference volume. From $N_D$ slices of RTV only $N_R$ slices are chosen and the rest are eliminated.

In further embodiments, such processing of the acquired data includes correcting for at least one of field of view, slice thickness and orientation. In yet further embodiments, the imaging technique is one of a MRI, CT, X-ray, PET and UT imaging technique In yet further embodiments, such acquiring image data includes acquiring image data of a given region of interest using one imaging technique and acquiring image data again for the given region of interest using a second imaging technique and wherein such processing includes processing the acquired image data from both imaging techniques so that the image data of said one technique is co-registered with the acquired data using the second imaging technique. In addition, said one imaging technique is one of a MRI, CT, X-ray, PET and UT imaging technique and the second imaging technique is the other of an MRI, CT, X-ray, PET and UT imaging technique.

In yet further embodiments, such acquiring image data includes acquiring image data for a given region of interest using one imaging technique and acquiring another image data for the given region of interest using the one imaging technique; wherein such processing includes processing the acquired image data for the one and the another imaging data. The imaging technique is one of a MRI, CT, X-ray, PET and UT imaging technique.

In yet further aspects/embodiments of the present invention, there is featured a system for registration of multiparametric and modality images or objects, comprising one of a a microprocessor, digital signal processor or ASIC; and a software program for execution on said one of the microprocessor, digital signal processor or ASIC. Such a software comprises program comprising code elements, criteria and instructions in a form that instructs said one of the microprocessor, digital signal processor or ASIC to perform functions of processing acquired image data. Such processing of image data comprises resizing number of slices in one of a plurality of planes or all planes to a desired size using orthogonal reslicing and to obtain resampled target volume (RTV), registration parameters estimation based on non-uniform radial reslicing: searching for best match between reference slices and resampled target volume (RTV) slices, and non-uniform radial reslicing comprising (i) 3D rotation, (ii) slice-by-slice affine transformation (translation and scale only) of the resampled target volume (RTV), and (iii) search which slices of RTV, after applying (i) and (ii), are similar to or very similar to slices of the reference volume.

In further embodiments, the 3D rotation angles are defined by the relationship ($\phi$, $\theta$ and $\psi$), where $\phi$, $\theta$ and $\psi$ can be between −90 and 90 degree. Also, the reslicing plane is one of axial, coronal and/or sagittal.

In yet further embodiments such non-uniform radial resampling comprises 3D affine transforms ($A = \{a_i\}_{i=1:NR}$) to select some of slices of resampled target volume (RTV), obtained by 3D resampling of the target volume to a spatial resolution higher than spatial resolution of the reference volume, in a non-uniform manner, such a 3D affine transform including parameters of 3D rotations, translation and scaling estimated using an optimization search routine.

In yet further embodiments, such processing of the acquired data includes correcting for at least one of field of view, slice thickness and orientation.

In yet further embodiments, such an imaging technique is one of a MRI, CT, X-ray, PET and UT imaging technique In yet further embodiments, the acquired image data comprises image data of a given region of interest using one imaging technique and image data for said given region of interest using a second imaging technique and wherein said processing includes processing the acquired image data from both imaging techniques so that the image data of said one technique is co-registered with the acquired data using said second imaging technique. Also, said one imaging technique is one of a MRI, CT, X-ray, PET and UT imaging technique and wherein said second imaging technique is the other of an MRI, CT, X-ray, PET and UT imaging technique.

In yet further embodiments, the acquired image data includes one set of image data of a given region of interest using one imaging technique and another set of image data for said given region of interest using said one imaging technique; wherein said processing includes processing the acquired image data for said one and said another imaging data, and wherein said imaging technique is one of a MRI, CT, X-ray, PET and UT imaging technique.

In yet further aspects/embodiments of the present invention, there is featured a system for 3D registration of multiparametric and modality images or objects, comprising one of a a microprocessor, digital signal processor or ASIC and a software or applications program for execution on said one of a a microprocessor, digital signal processor or ASIC. Such a software program includes program code elements, criteria and instructions in a form that instructs the one of a a microprocessor, digital signal processor or ASIC to perform functions of processing acquired image data. Such processing includes resampling the target image volume to a desired size using orthogonal resampling (reslicing), name new target volume as resampled target volume (RTV), and non-uniform resampling: search which slices of RTV are match with which slices of the reference volume and what 3D affine transforms make those matching possible. Such a 3D affine transform is defined by $A = \{a_i\}_{i=1:NR}$ with parameters of $\phi_i$, $\theta_i$, $\psi_i$, translation ($h_i$) and scale ($s_i$) and in more particular embodiments the estimated 3D rotation angles ($\phi_i$, $\theta_i$, and $\psi_i$) can be between −90 and 90 degree.

In further embodiments such processing of the acquired data includes correcting for at least one of field of view, slice thickness and orientation and where the imaging technique is one of a MRI, CT, X-ray, PET and UT imaging technique In yet further embodiments, the acquired image data comprises image data for a given region of interest using one imaging technique and image data for said given region of interest using a second imaging technique and wherein such processing includes processing the acquired image data from both imaging techniques so that the image data acquired using one technique is co-registered with the image data acquired using the second imaging technique. Also, the one imaging technique is one of a MRI, CT, X-ray, PET and UT imaging technique and wherein the second imaging technique is the other of an MRI, CT, X-ray, PET and UT imaging technique.

In yet further embodiments, the acquired image data includes one set of image data for a given region of interest acquired using one imaging technique and another set of image data acquired for the given region of interest using that one imaging technique. Such processing also includes processing the acquired image data for the one and another imaging data, and wherein the one imaging technique is one of a MRI, CT, X-ray, PET and UT imaging technique.

According to yet other aspects of the present invention the above described methods and systems are implemented or carried out on a computer including an applications programs having instructions, criteria and code segments for performing the methods of the present invention. Also featured is a computer readable storage medium on which is stored such an applications program.

Other aspects and embodiments of the invention are discussed below.

Definitions

The instant invention is most clearly understood with reference to the following definitions:

As used in the specification and claims, the singular form "a", "an" and "the" include plural references unless the context clearly dictates otherwise.

As used herein, the term "comprising" or "including" is intended to mean that the compositions, methods, devices, apparatuses and systems include the recited elements, but do not exclude other elements. "Consisting essentially of", when used to define compositions, devices, apparatuses, systems, and methods, shall mean excluding other elements of any essential significance to the combination. Embodiments defined by each of these transition terms are within the scope of this invention.

The term ASIC as used in the specification and claims shall be understood to mean application specific integrated circuit.

The term DCE-MRI as used in the specification and claims shall be understood to mean Dynamic Contrast Enhanced MRI.

Radiological images as used in the specification and claims shall be understood to mean images or image data acquired using MRI, X-Ray, CT, PET or UT imaging techniques.

A computer readable medium shall be understood to mean any article of manufacture that contains data that can be read by a computer or a carrier wave signal carrying data that can be read by a computer. Such computer readable media includes but is not limited to non-transitory media such as magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; paper media, such as punched cards and paper tape; or carrier wave signal received through a network, wireless network or modem, including radio-frequency signals and infrared signals.

USP shall be understood to mean U.S. patent Number, namely a U.S. patent granted by the U.S. Patent and Trademark Office.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 2A, B are illustrative views showing reslicing types: orthogonal vs. angular volume reslicing. In orthogonal reslicing (FIG. 2A), the slices are parallel to the reslicing plane and in angular reslicing (FIG. 2B), the slices have an angle with the reslicing plane.

FIG. 4A—signal downsampling using 1D-Discrete Wavelet Transform (DWT)

FIG. 5 is a block diagram/high level flow diagram of a pipeline and steps: 1) orthogonally reslicing target volume to a spatial resolution L($>=2$) times bigger than spatial resolution of the reference volume and name resultant resampled target volume (RTV), which has $N_D = L*N_R$ slices, where $N_R$ is number of slices if the reference volume and L is a user defined control parameter to control ratio of resolution increase of target volume compared to the reference volume; 2) searching for optimized 3D affine transforms which makes $N_R$ out of $N_D$ slices of RTV very similar to reference volume slices, which has $N_R$ slices. In this search to rotate RTV in 3D, Euler angles ($\phi$, $\theta$ and $\psi$) are varied from $-\alpha$ to $+\alpha$ to get $3*\alpha$ volumes (total number of slices are K=NR*3*$\alpha$ Slices), where $\alpha$ is a user defined control parameter to control degree of rations of RTV in 3D and $\alpha$ can have any value between −90 to +90 degree. All of K slices driven by rotating RTV in 3D are used to search for an optimized translation and scaling of those K slices using a method named similarity maximized transform (SMT), which is based on least square optimization.

FIG. 7 provides pictorial views of seven typical slices from registered in-vivo and ex-vivo T2-weighted image volumes. Both in-vivo and ex-vivo image volumes were in the axial plane and there was no need to apply step 1 in FIG. 1 to transfer volumes to the desired plane, which was axial plane. The in-vivo image volume was chosen as the reference volume. The ex-vivo image volume was chosen as the target volume. User defined control parameters were L=2 and $\alpha$=10 degree. In the radial reslicing step (FIG. 5), the estimated rotation angles to register all slices of ex-vivo data with in-vivo were around $\phi$=0, $\theta$=2.5 and $\psi$=0 (2.5 degree in sagittal plane) for all slices because a prostate is a rigid object. In the first three register ex-vivo slices, a portion of images is vanished due to lack of data after rotation for interpolation.

FIG. 8 provides pictorial views of typical ex-vivo images: a) Original images: T2-WI and DWI (b=50,400,800 and ADC). After registering ex-vivo data with T2-WI in-vivo by method and steps shown in FIG. 5, an additional step was needed to be done on DWI ex-vivo data due to a severe localized geometric distortion induced by the echo planar imaging (EPI) technique. In this additional step, reference and target volumes were transferred to the coronal plane and for each slice in the coronal plane method and steps shown in FIG. 5 was used to correct distortion.

DESCRIPTION OF THE PREFERRED EMBODIMENT

As described further herein, by using the registration methods and systems of the present invention complementary information between radiological images and histopathology are obtained allowing for co-registration and warping in 3D. More particularly, a 3D registration methodology based on non-uniform reslicing of the target and reference image volumes is described/introduced herein. The following discussion provides/describes methods, systems and material according to the present invention.

In the following discussion reference is made to block diagrams or high level flow diagrams that illustrate various methodologies for registering and/or reconstructing images according to the present invention. The flow charts/diagrams or block diagrams herein illustrate the structure of the logic of the different methodologies/inventions, which can be embodied in a computer program software for execution on a computer, digital processor, microprocessor or application specific integrated circuit (ASIC). Those skilled in the art will appreciate that the flow charts/diagrams and/or block diagrams illustrate the structures of the computer program code elements, including logic circuits on an integrated circuit, that function according to the present inventions. As such, the present inventions also are practiced in its essential embodiments by a machine component that renders the program code elements in a form that instructs a digital processing apparatus (e.g., computer) to perform a sequence of function step(s) corresponding to those shown in the flow diagrams. Reference in the specification or claims to one of a computer, digital processor, microprocessor or ASIC shall be understood to also include any of the other of computer, digital processor, microprocessor, ASIC or the like.

3D Registration

Registration of two image volumes is the determination of a geometrical transformation or mapping from points in one image volume to points in another image volume. If the transformation is accurate, the registered image slices can be used for the post-processing steps such as image subtraction, volumetric analysis, matching image voxel locations with the histological data, tissue characterization and segmentation. There are two types of registration: 1) rigid (non-deformable) and 2) non-rigid (deformable) transformations. In most cases one has 3D deformation and warping in the multimodal images, so one uses the second type of registration method which is compatible with multimodal/multiparametric images and works in 3D.

Figure 1:
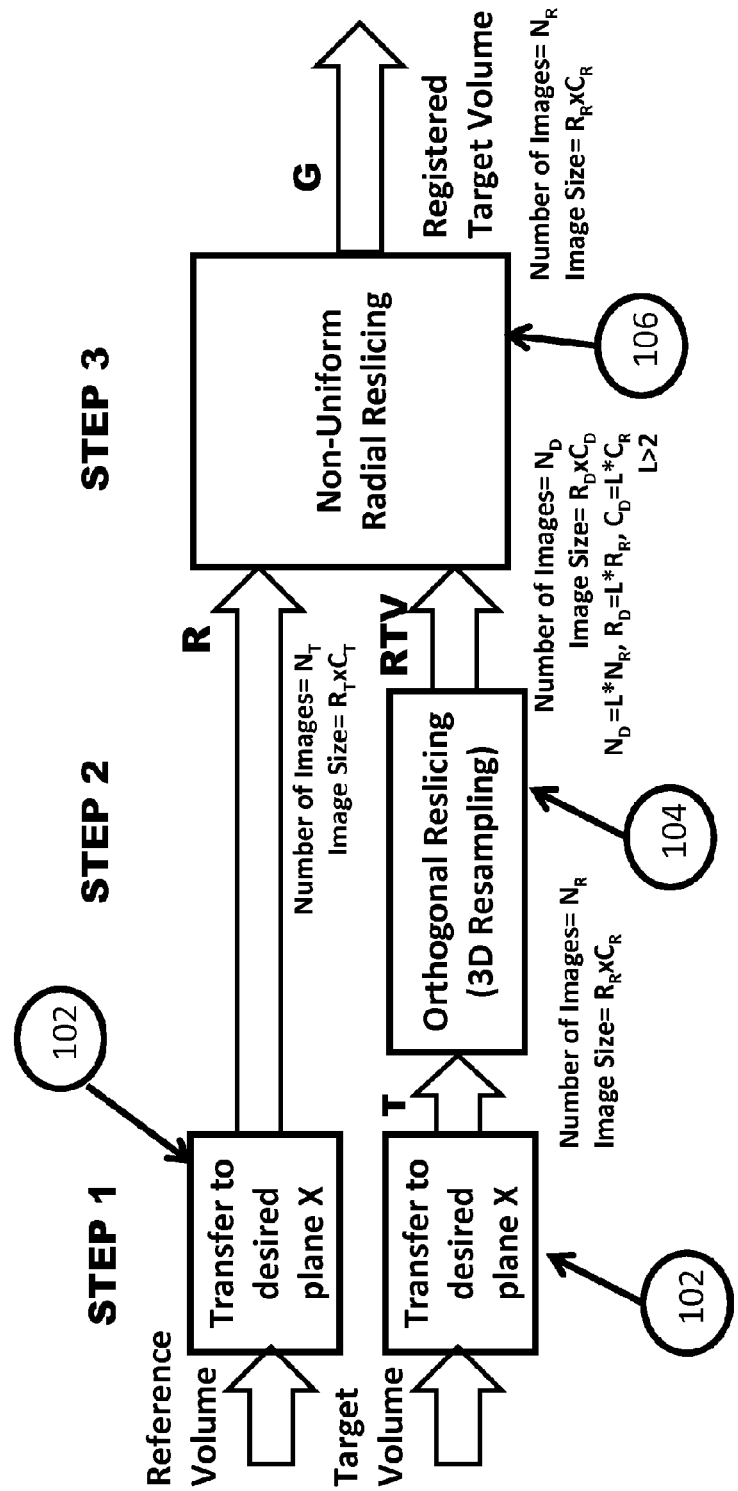
FIG. 1 is a block diagram for 3D registration of the reference and target volumes based on volume reslicing. First step is to transfer reference and target volumes to the desired plane X. X can be Axial, Coronal and Sagittal. The transferred reference and target volumes respectively named R and T. Second step is for orthogonally re-slice the volume T to make resampled target volume (RTV). The third step is a 3D affine transform. Step 2 followed by step 3 is a radial volume reslicing.

The novel 3D registration technique of the present invention is based on reslicing of the target volume to the reference volume. As shown in FIG. 1, the registration method according to the present invention includes three general steps: 1) transferring reference and target volumes to the desired plane x, which is one of axial, sagittal or coronal planes —Steps 102; 2) Orthogonal reslicing: uniform resampling of target volume to obtain a volume named resampled target volume (RTV) which has a resolution L times higher than spatial resolution of the reference volume—Step 104; 3) Non-uniform radial resampling—Step 106: search which slices of RTV are matched with which slices of the reference volume and what 3D affine transforms make those matching possible. Such a 3D affine transform is defined by $A=\{a_i\}_{i=1:NR}$ with parameters of 3D rotations ($\phi_i$, $\theta_i$, $\psi_i$), translation ($h_i$) and scale ($s_i$) and in more particular embodiments the estimated 3D rotation angles ($\phi_i$, $\theta_i$ and $\psi_i$) can be between −90 and 90 degree.

Reslicing (Resampling)

In most cases, the number of slices and image (matrix) size for the reference and target volumes are different. Target volume is a volume that one wants to register it with the reference volume. In the present invention a 3D resampling scheme is sued to resize images and change number of slices in the target volume. Resampling of a discrete signal f[n] is defined as changing number of signal samples, where n is the sample index. There are two types of resampling: upsampling and downsampling. If number of samples in f[n] is increased using zero padding or interpolation, it is called upsampling. If the number of samples in f[n] is decreased, it is called downsampling. However, downsampling may cause losing spatial and textural information. To avoid this problem, a powerful multi-resolution analysis called wavelet transform (Mallat 2008) was used, which is explained in the next section.

Figure 3A:
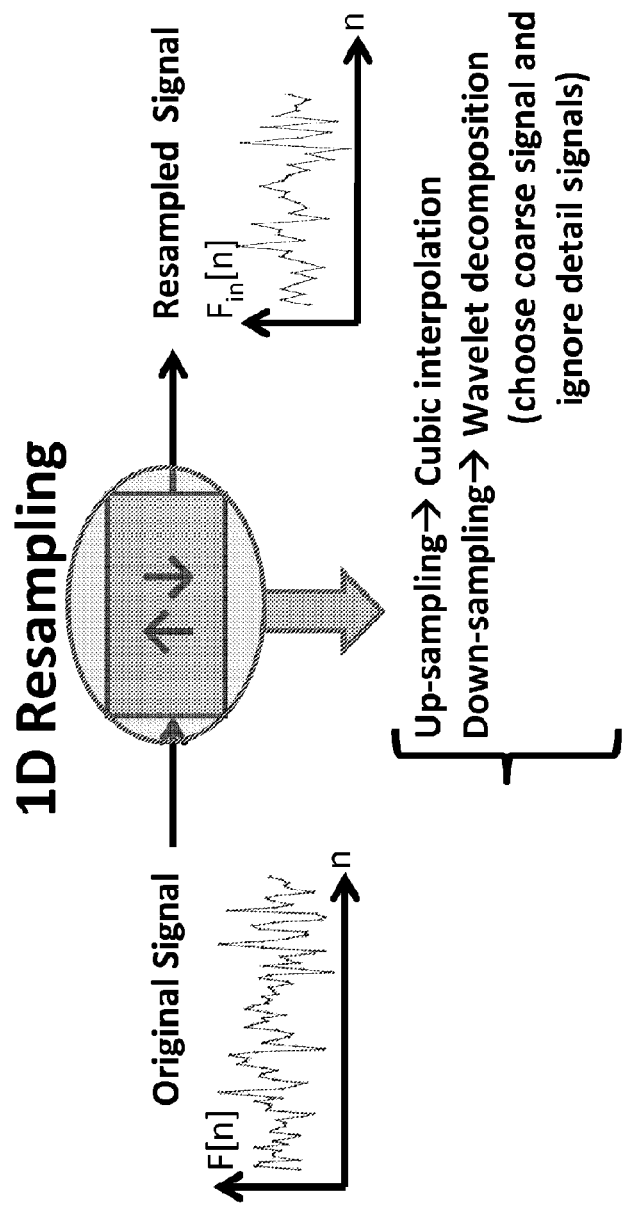
FIGS. 3A,B and C respectively illustrate 1D, 2D and 3D resampling schemes. If desired number of samples in any of dimension (rows, columns or along slices) is higher than original number of samples, it is named upsampling and interpolation is used. If desired number of samples any of dimension (rows, columns or along slices) is lower than original number of samples, it is named downsampling and wavelet decomposition is used.
Figure 3B:
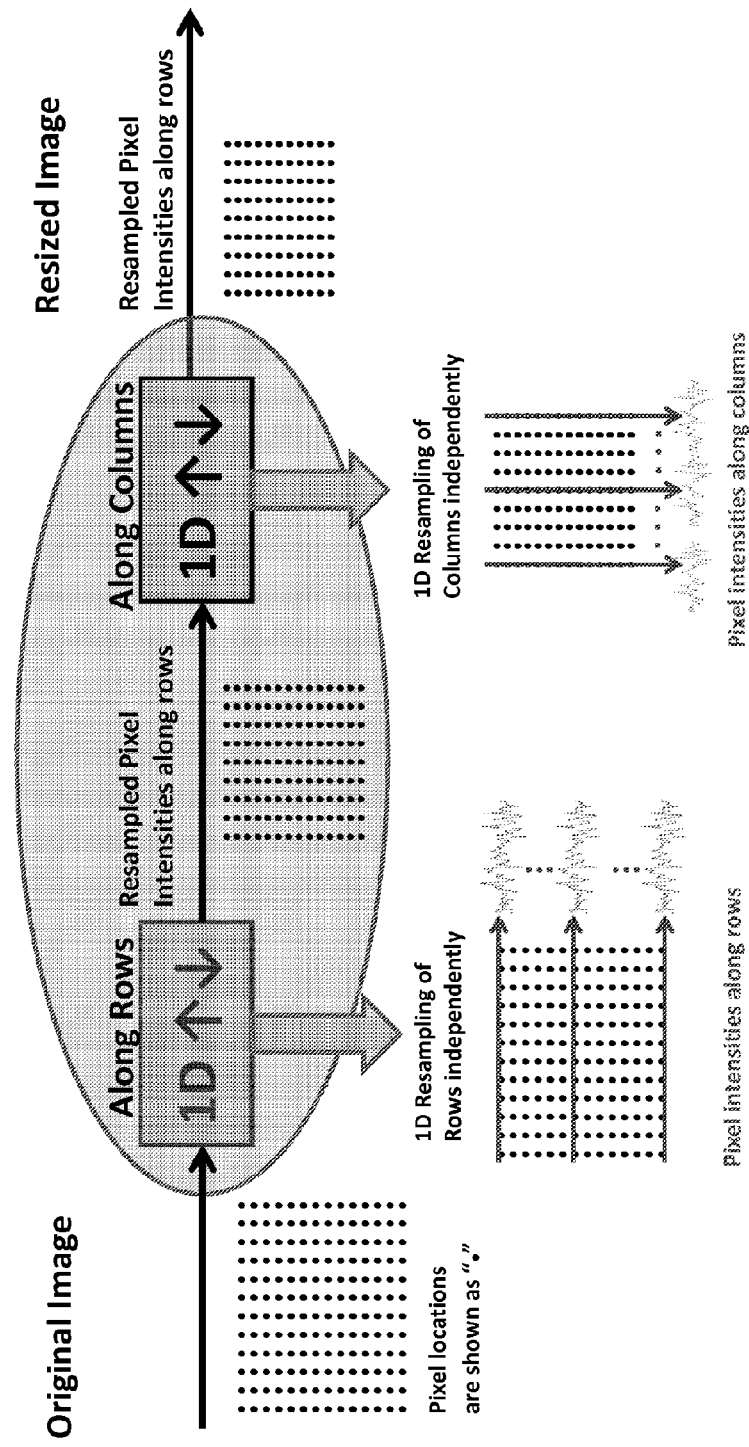
Figure 3C:
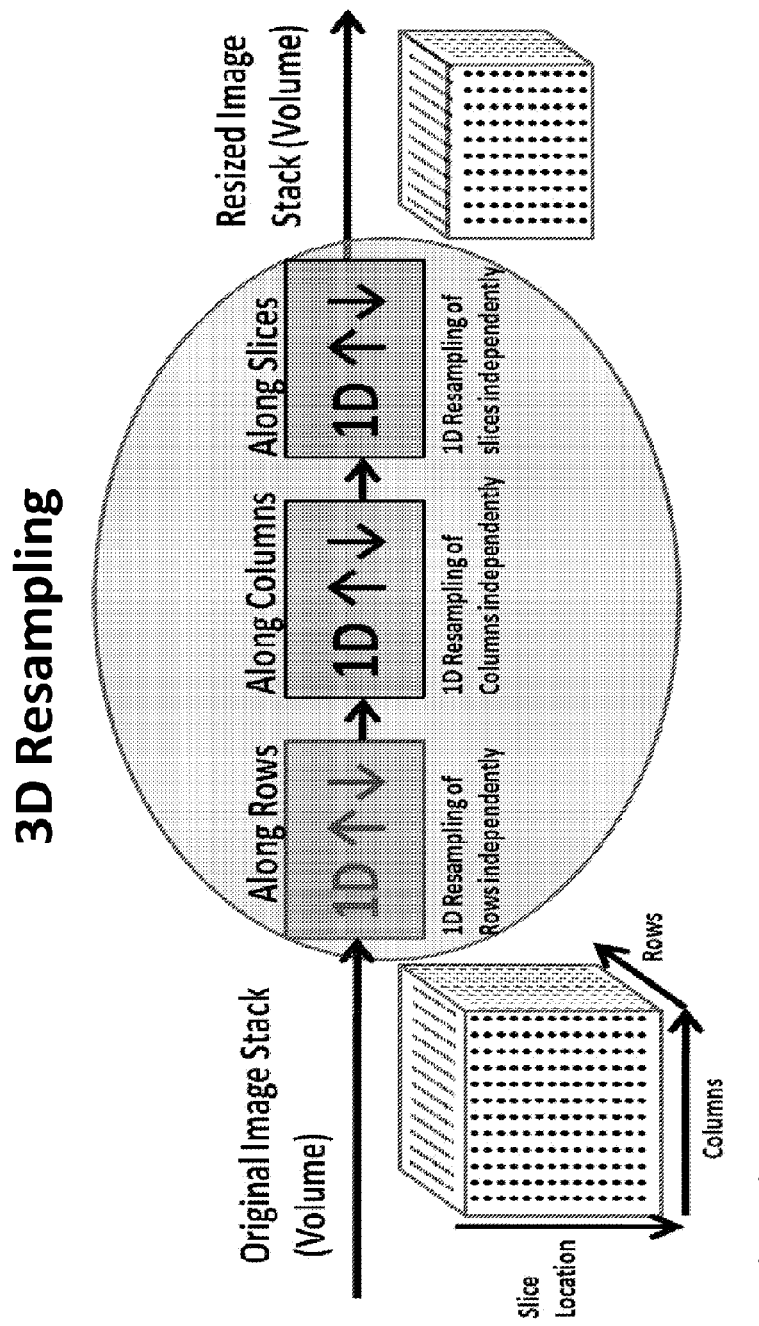

FIG. 3(a) shows 1D resampling schema to resample a target signal F[n] to a resampled signal $F_{in}$[n]. To perform a 2D resampling and resize an image, 1D resampling is applied along rows and then along columns, where each pixel in the image is defined a sample and pixel position in the image is the sample row and column indices. As shown in FIG. 3(b), 1D resampling is first applied along each row of the image. When 1D resampling of rows are done, 1D resampling is then applied along each column of the image. After 1D resampling of columns are done, the resultant is the resized image. In 3D resampling, similar to 2D resampling, the resampling is done by applying 1D resampling sequentially along three resampling axes: rows, columns and slices. FIGS. 3(b) and 3(c) respectively show 2D and 3D resampling schemes.

In the above volume (3D) resampling technique, the resampling axes are perpendicular to one of axial, coronal or sagittal planes, and therefore it is called "orthogonal resampling". However if there is an angle (θ), less than 90 degree, between the resampling axes and one of axial, coronal or sagittal planes, it is called "radial resampling" and it is done by applying the orthogonal resampling, 3D, followed by a 3D rotation of volume. The rotation of a volume is done using Eulerangles (φ, θ, ψ) which are three angles to describe the orientation of a rigid body.

The following rotation matrix rotates the image volume about the rows, columns and slice axes:

$$R_\phi = \begin{bmatrix} \cos(\phi) & 0 & -\sin(\phi) \\ 0 & 1 & 0 \\ \sin(\phi) & 0 & \cos(\phi) \end{bmatrix} \quad (1)$$

$$R_\theta = \begin{bmatrix} 1 & 0 & 0 \\ 0 & \cos(\theta) & \sin(\theta) \\ 0 & -\sin(\theta) & \cos(\theta) \end{bmatrix}$$

$$R_\psi = \begin{bmatrix} \cos(\psi) & \sin(\psi) & 0 \\ -\sin(\psi) & \cos(\psi) & 0 \\ 0 & 0 & 1 \end{bmatrix}$$

The first rotation is by an angle φ∈[0,2π] about the z-axis using $R_\phi$. The second rotation is by an angle θ∈[0, π]αout the former x-axis (now x') using $R_\theta$. The third rotation is by an angle ψ∈[0, 2π] about the former z-axis (now z') using $R_\psi$. This yields flowing 3D rotation matrix:

$$R = R_\phi * R_\theta * R_\psi \quad (2)$$

Figure 2:
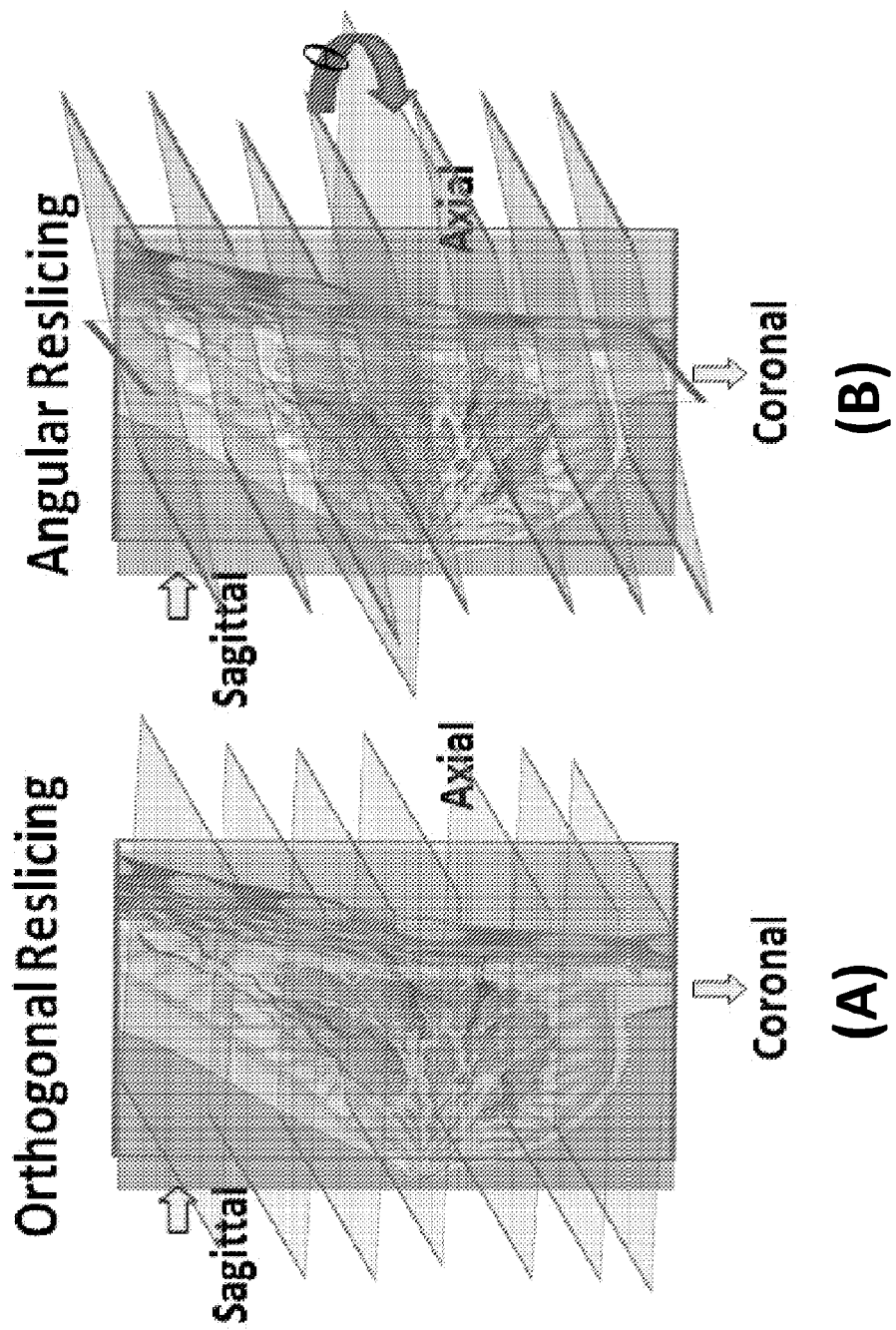
FIGS. 2A and 2B respectively show orthogonal and angular (radial) volume reslicing types. For second step see FIGS. 3 and 4. For the third step see FIG. 6.

FIGS. 2(a) and 2(b) respectively show 2D and 3D radial resampling schemes. In both schemes data in 2D or 3D is first rotated and then 2D or 3D orthogonal resampling is applied as described above and in FIGS. 1(b) and 1(c).

Wavelet Transform, a Multi-Resolution Analysis:

The wavelet transform of a square-integrable function f(x), is defined as $$wf(s, x) = \int_{-\infty}^{\infty} f(x) \frac{1}{\sqrt{s}} \psi\left(\frac{x-\tau}{s}\right) d\tau \quad (3)$$

where s and x are the scale (or frequency) and pixel location along resampling plane, respectively. The function ψ(x), called wavelet, must satisfy the admissibility condition, i.e., it must be a zero-mean, square-integrable function. By use of wavelet function, wavelets (bases)

$$\frac{1}{\sqrt{s}} \psi\left(\frac{x-\tau}{s}\right)$$

are defined as functions whose translations and dilations are used for expansions in Hilbert space $L^2$ ($\Re$). In practical applications, to allow fast numerical implementation, we impose that scale parameter s varies only along dyadic sequence $(2^j)_{j \in Z}$ where the set of integers forms a ring that is denoted z.

Wavelet function can be generated by integer translations of a function called scaling function φ(x) and a sequence of real numbers h[n] and g[n] such that [33]:

$$\frac{1}{\sqrt{2}} \psi\left(\frac{x}{2}\right) = \sum_{n=-\infty}^{+\infty} g[n]\phi(x-n) \quad (4)$$

$$\frac{1}{\sqrt{2}} \phi\left(\frac{x}{2}\right) = \sum_{n=-\infty}^{+\infty} h[n]\phi(x-n)$$

It is proved that h[n] and g[n] are conjugate mirror filters, which means:

$$|\hat{h}(\omega)|^2 + |\hat{h}(\omega + \pi)|^2 = 2 \quad (5)$$

$$|\hat{g}(\omega)|^2 + |\hat{g}(\omega + \pi)|^2 = 2$$

Filter h[n] acts as a low-pass filter and hence only low-frequency (coarse) information can pass through it; on the other hand g[n] is a high-pass filter to pass high frequency (detail) information. Filters h[n] and g[n] entirely determine the scaling function φ(x) and most of its properties. If h[n] and g[n] have a finite number of nonzero coefficients, said to be Finite Impulse Response (FIR) filters, the scaling function φ(x) is compactly supported, which means it is zero outside of a compact set. A set S of real numbers is called compact if every sequence in S has a subsequence that converges to an element again contained in S.

Figure 4A:
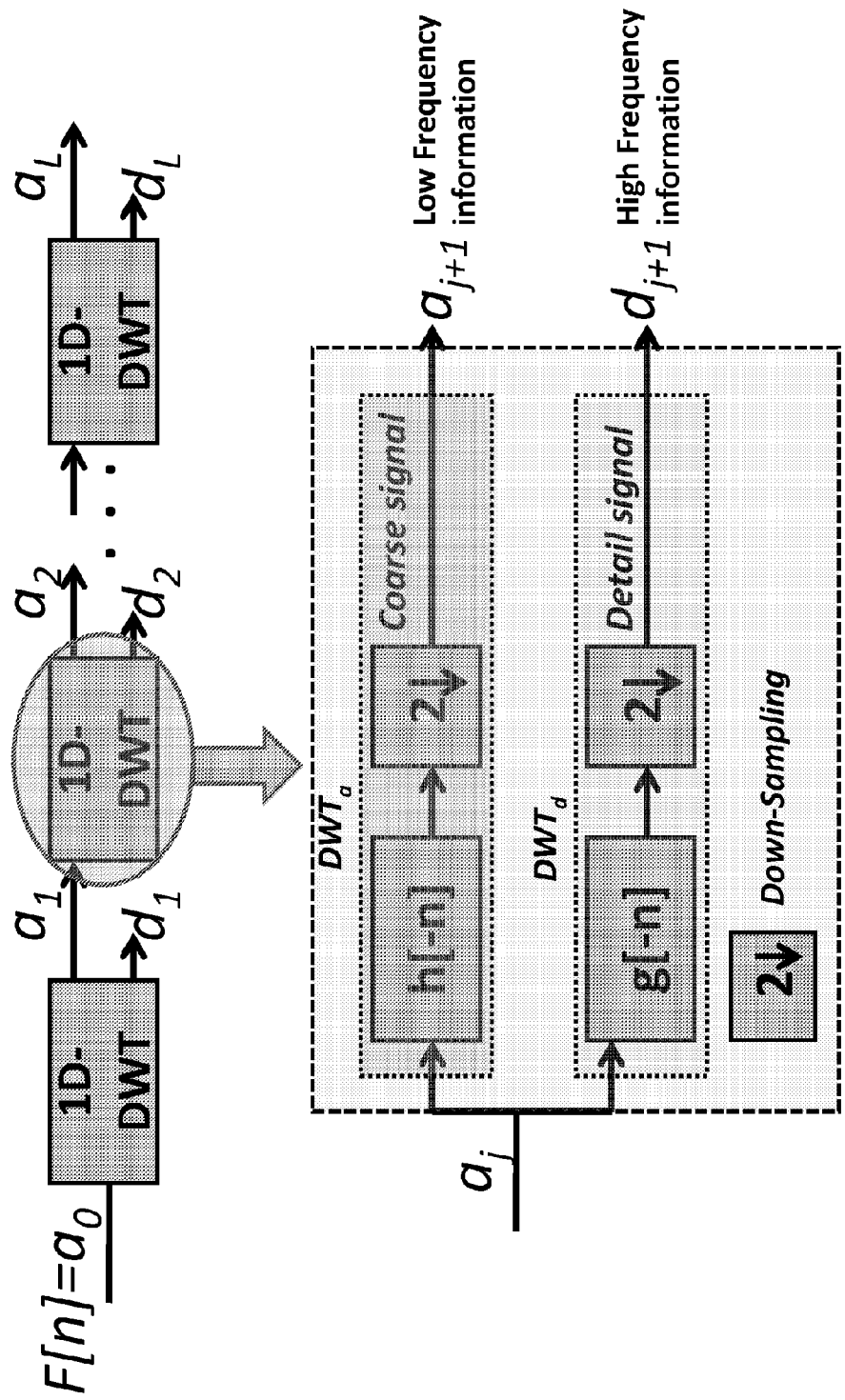
FIGS. 4A, B and C respectively illustrate 1D, 2D and 3D wavelet transform based downsampling schemes.
Figure 4B:
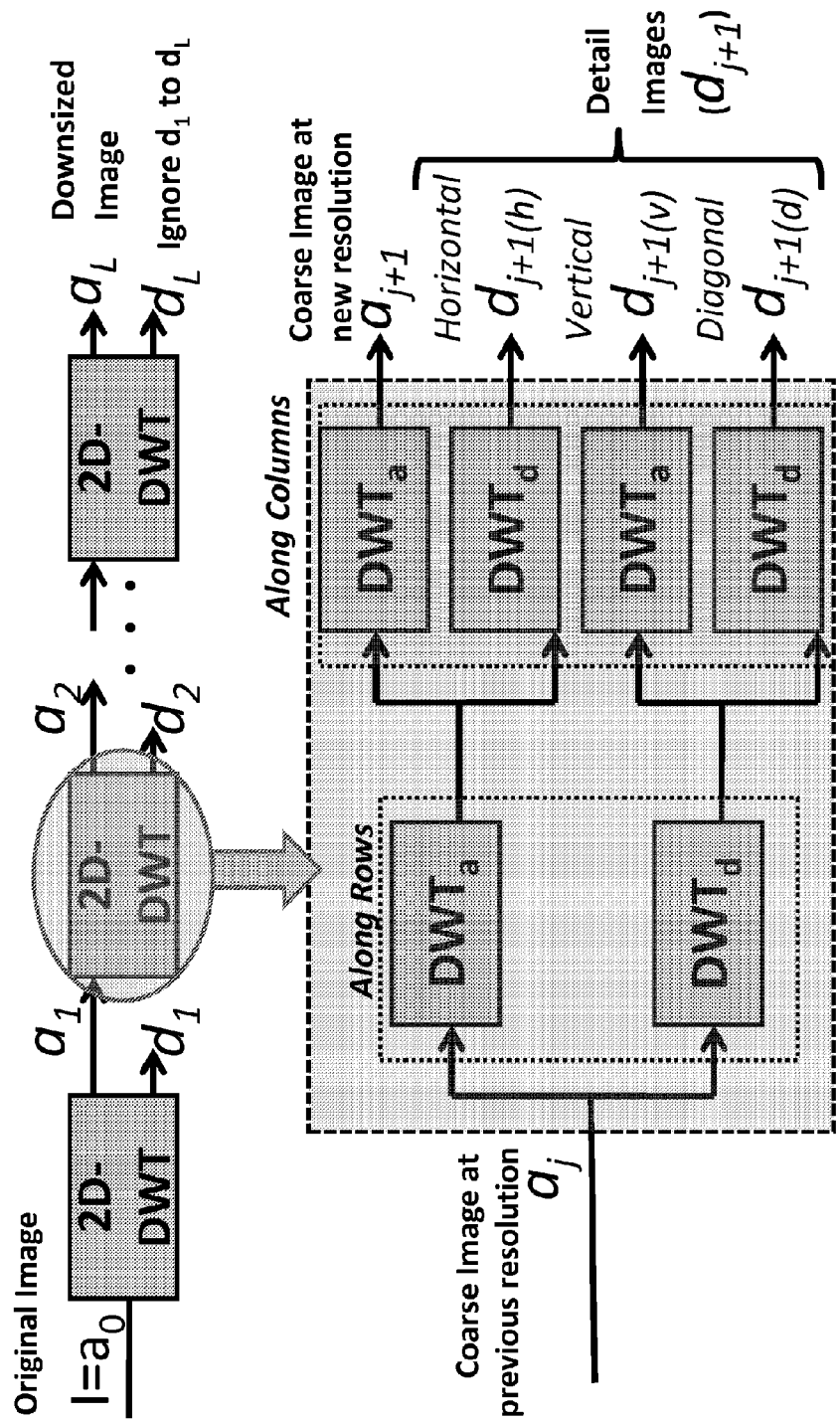
FIG. 4B—image downsizing using 2D-Discrete Wavelet Transform (DWT)
Figure 4C:
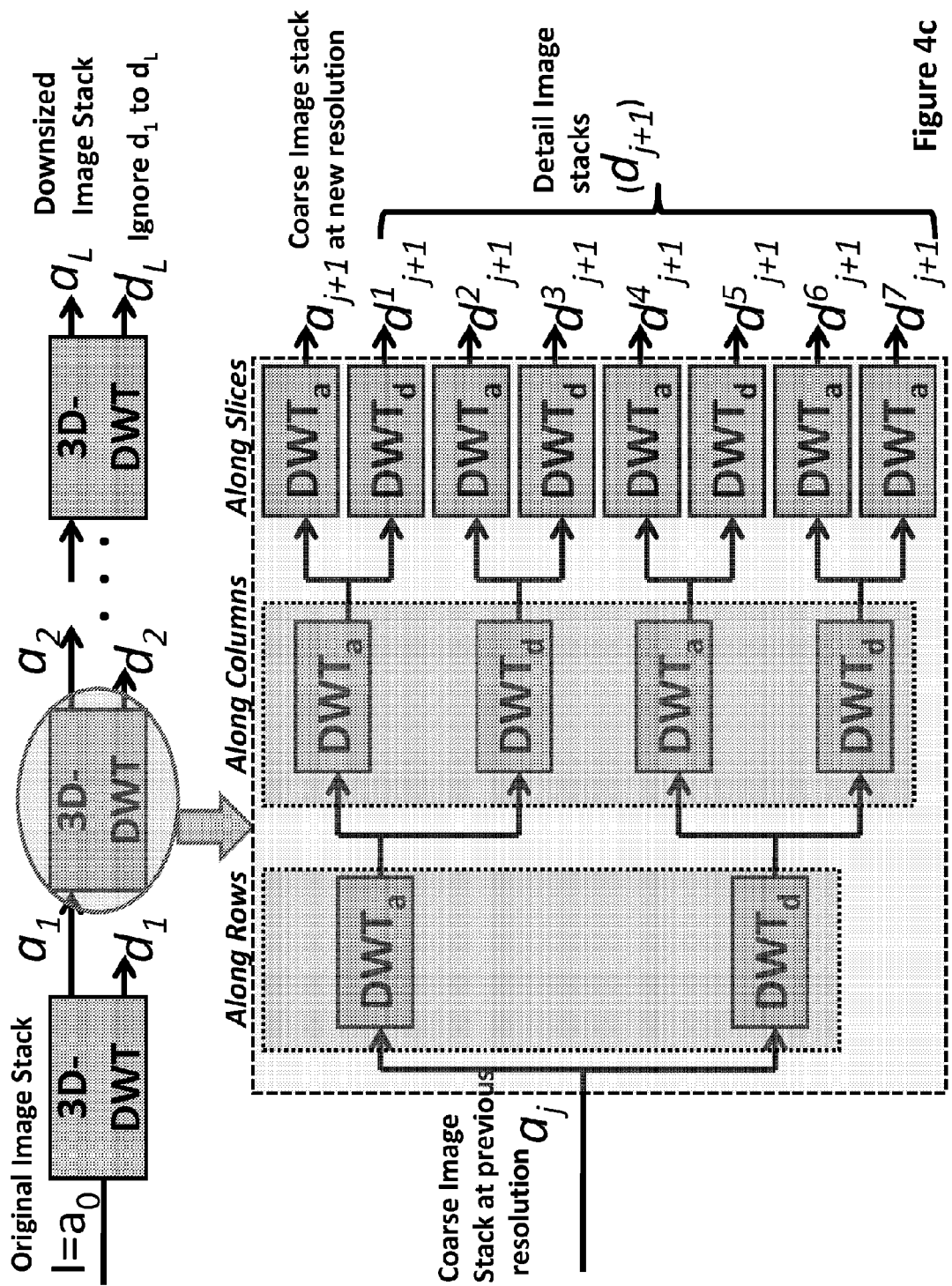
FIG. 4C—volume downsizing using 3D-Discrete Wavelet Transform (DWT). in volume reslicing (3D resampling), based on how many dimensions need to be downsized, one or combinations of schemes shown in FIGS. 4A, B and C are used. If all three dimensions (rows, columns and along slices) need to be downsized, method in FIG. 4C is used. If two dimensions need to be downsized, combination of method in FIG. 4B and method in FIG. 3A with interpolation is used. If one of dimensions need to be downsized, combination of method in FIG. 4A and method in FIG. 3B with interpolation is used. If none of dimensions need to be downsized, method in FIG. 3C with interpolation is used.

It is proved that there exists some particular basis functions called orthogonal wavelet bases $$\frac{1}{\sqrt{2^j}} \psi\left(\frac{x-n}{2^j}\right)$$

such that $(\sqrt{2^{-j}}\psi(2^{-j}x-n))_{(j,n) \in Z}$ is an orthonormal (orthogonal and unit length) basis of Hilbert space $L^2(\Re)$. If filters h[n] and g[n] are driven from such an orthogonal wavelet and scaling functions, we could then decompose the signal to a series of low frequency (a) and high frequency components (d) and then reconstruct the signal using those components:

$$a_0 = f(x)$$

$$a_j[n] = a_{j-1}[n] * h[-2n], d_j[n] = a_{j-1}[n] * g[-2n] \forall j \in Z$$

$$\hat{a}_{j-1}[n] = U(a_j[n]) * h[n] + U(d_j[n]) * g[n] \forall j \in Z \quad (6)$$

where U(x) denotes the signal obtained from x by inserting a zero between every sample and $\hat{a}_j$ is reconstructed version of $a_j$. h[2n] and g[2n] are down-sampled versions of h[n] and g[n] by downsampling factor of 2. If wavelets are orthogonal, the filter bank is said to be a perfect reconstruction filter bank and $\hat{a}_j = a_j$ Equation 6 is called fast wavelet transform (FWT) and leads us to the concept of multiresolution approximation (or multiresolution analysis) and consecutive approximations at finer and finer resolutions. FIG. 4(a) illustrates equation 6 using iterative filter banks. To obtain a 2D wavelet transform which can be used to resize an image, 1D wavelet is applied along rows and then along columns. After 1D resampling of columns are done, the resultant is the resized image. In 3D resampling, similar to 2D resampling, the resampling is done by applying 1D resampling sequentially along three resampling axes: rows, columns and slices. FIGS. 4(b) and 4(c) show 2D and 3D fast wavelet transforms, which are respectively used to downsize an image and a volume.

3D Registration Steps (See FIGS. 1 and 4)

A 3D multimodal registration technique employs iterative resamplings of the target volume slices to register target and reference volumes. As shown in FIG. 1, the 3D registration comprises three steps:

Step 1: transferring reference and target volumes to the desired plane x, which is one of axial, sagittal or coronal planes—Steps 102.

Step 2: Orthogonal reslicing: the 3D resampling, shown in FIG. 3c, is used to change the number of slices and image matrix size in target volume respectively from $N_T$ and $R_T \times C_T$ to $N_D$ and $R_D \times C_D$, which are equals to $N_D = L*N_R$, $R_D = L*R_R$, $C_D = L*C_R$. L is a user defined value, which we suggest to set it to at least 2. By applying this step a new target volume called resampled target volume (RTV) is obtained.

Step 3: Non-Uniform Radial Reslicing: We first rotate RTV with different rotation angles Θ, starting from −α and ending +α degrees (α∈[−90,90]) with step size of 1 degree to get a series of volumes, named RS. This routine of incremental 3D rotations generates 3*α slabs, a series of slabs called RS. Each slab itself has $N_D$ slices, therefore total number of slices is $3*\alpha*N_D$. By applying this step a set of target volumes called RS is obtained. $N_D$ is number of slices of volume RTV.

After applying iterative 3D rotations of RTV, an optimization search is used to find a best match for each slice of the reference volume. First, corresponding to first slice of the reference volume, $r_1$, L nearest slices are selected from each of RS slabs, therefore M=L*3*a slices are selected in total out of RS slabs. L is a user defined value, which is set it to at least 2 (see step 2). A least square based method named Similarity Maximized Transform (SMT), described herein, is used to find which one of M slices and with which translation and scale is very similar to $r_1$. This is done by looking at mean-square-error (MSE) and dice similarity (DS) between reference and target images, dice similarity (DS) is defined Dice similarity index is calculated:

$$DS = 2\frac{A \cap B}{A+B} \quad (7)$$

where A and B are respectively binary makes extracted from $r_1$ and a slice of RS volume. Between M slices driven from 3D iterative rotations of RTV, a slice of RTV with index $j_{optimized}$ that provides the highest DS and lowest MSE is chosen as the best match with reference slice $r_1$. The resultant is the image $g_1 = a(RTV(j_{optimized}))$, which has the highest similarity index and minimum mean-square-error with $r_1$. a(.) is the estimated 3D affine transform with parameters $(\phi_1, \theta_1$ and $\psi_1, h_1$ and $s_1$. To register with all slices of the reference volume, repeat this search routine $N_R$ times to get an image volume of $G = \{g_i\}_{i=1:NR}$ obtained using estimated affine transforms $A = \{a_i\}_{i=1:NR}$ which is the registered volume with the reference volume R in 3D. $N_R$ is number of slices for the reference volume. From $N_D$ slices of RTV only $N_R$ slices are chosen and rest are eliminated. FIG. 5 illustrates the routine for step 3.

Similarity Maximized Transform (SMT)

SMT is a method to find transformation (translation and scale only) between the target image $I_T$ and reference image $I_R$ and has two steps: suppose $I_R$ and $I_T$ has a matrix (image) size of N1×N2. In the first step, images are converted to L binary images ($\{B_i^R\}_{i=1:L1}$ and $\{B_j^T\}_{j=1:L2}$) using multilevel Otsu thresholding, a threshold selection method from gray-level histograms. Number of levels respectively are L1 for $I_R$ and L2 for $I_T$. The following affine transform is then applied:

$$B_{L_1,i}^R(x,y) = B_{L_2,j}^T(s_{x,L1,L2,i,j}*x + h_{x,L1,L2,i,j}, s_{y,L1,L2,i,j}*y + h_{y,L1,L2,i,j}), \forall i=1:L_1, \forall j=1:L_2 \quad (8)$$

where x and y are pixel locations and $s_i=[s_x,s_y]$ and $h_i=[h_x,h_y]$ respectively are scale and translation parameters of affine transformation. i and j respectively are image number from image stack of $\{B_i^R\}_{i=1:L1}$ and image stack of $\{B_j^T\}_{j=1:L2}$. i and j indeed shows which binary image of the reference binary images ($\{B_i^R\}_{i=1:L1}$) match with which binary image of the reference binary images ($\{B_j^T\}_{j=1:L2}$). Control parameters s, h, $L_1$, $L_2$, i and j are estimated using our proposed optimization method driven from modifying and extending of linear robust least square optimization to minimize the following cost function:

$$\sum_{L1=2}^{10}\sum_{L2=2}^{10}\sum_{i=1}^{L1}\sum_{j=1}^{L2}\sum_{x=1}^{N1}\sum_{y=1}^{N2} w_{x,y,L1,L2,i,j}(B_{L1,i}^R(x,y) - B_{L2,j}^T \quad (9)$$

$$(s_{x,L1,L2,i,j}*x + h_{x,L1,L2,i,j}, s_{y,L1,L2,i,j}*y + h_{y,L1,L2,i,j}))$$

where $w_{x,y,L1,L2,i,j}$ are weights. The reason a robust least square is used instead of a standard least square is sensitivity of the standard least-squares optimization (fitting) to outliers. Outliers have a large influence on the optimization because squaring the residuals magnifies the effects of these extreme data points. To minimize the influence of outliers, a robust least-squares regression uses bisquare weights to minimize a weighted sum of squares, where the weight given to each data point depends on how far the point is from the fitted line. Points near the line get full weight. Points farther from the line get reduced weight. Points that are farther from the line than would be expected by random chance get zero weight.

A robust least square optimization with bisquare weights is an iteratively reweighted least-squares algorithm, has following iterative steps:

1) Fit the model by minimization of weighted least squares solution in Eq.9. If it is a first iteration set all weight to 1.

2) Compute the adjusted residuals. The adjusted residuals are given by $$res_{adjusted}(x, y, L_1, L_2, i, j) = \frac{res(x, y, L_1, L_2, i, j)}{\sqrt{1 - h(x, y, L_1, L_2, i, j)}}, \quad (10)$$

$$\forall x = 1:N_1, \forall y = 1:N_2, \forall L_1 = 2:10,$$

$$\forall L_2 = 2:10, \forall i = 1:L_1, \forall j = 1:L_2$$

res and h respectively are the usual least-squares residuals and leverages to adjust the residuals by reducing the weight and effect of high-leverage data points.

3) Normalize adjusted residuals by median absolute deviation of the residuals:

$$u_{x,y,i,j} = \frac{res_{adjusted}(x, y, L_1, L_2, i, j)}{c * MaD}, \quad (11)$$

$\forall x = 1:N_1, \forall y = 1:N_2, \forall L_1 = 2:10,$ $\forall L_2 = 2:10, \forall i = 1:L_1, \forall j = 1:L_2$ c is a tuning constant, and MaD is the median absolute deviation of the residuals.

4) Compute the bisquare weights:

$$w_{x,y,L1,L2,i,j} = \begin{cases} (1 - u_{x,y,L1,L2,i,j}^2)^2 & |u_{x,y,L1,L2,i,j}| < 1 \\ 0 & |u_{x,y,L1,L2,i,j}| \geq 1 \end{cases}, \quad (12)$$

$\forall x = 1:N_1, \forall y = 1:N_2,$ $\forall L_1 = 2:10, \forall L_2 = 2:10, \forall i = 1:L_1, \forall j = 1:L_2$ 5) If the fit converges, stop, else, repeat the next iteration by returning to the first step.

After obtaining control parameters (s, h, $L_1$, $L_2$, i, j,) using robust least square optimization, the estimated control parameters are used to get registered version of $I_T$. To evaluate registration accuracy, two parameters, mean-square-error (MSE) and dice similarity (DS) index, defined in Eq. 7 are calculated, and they are reported to step 3 of 3D registration: optimization search routine (see FIG. 5).

EXAMPLE

Using the methodology described herein, and evaluation was made to test performance as to how the methodology or technique of the present invention performs in registration of in-vivo image date with ex-vivo data. The results of this are reported below.

Results

Registration of In-vivo with Ex-vivo Data for the Prostate

Figure 6:
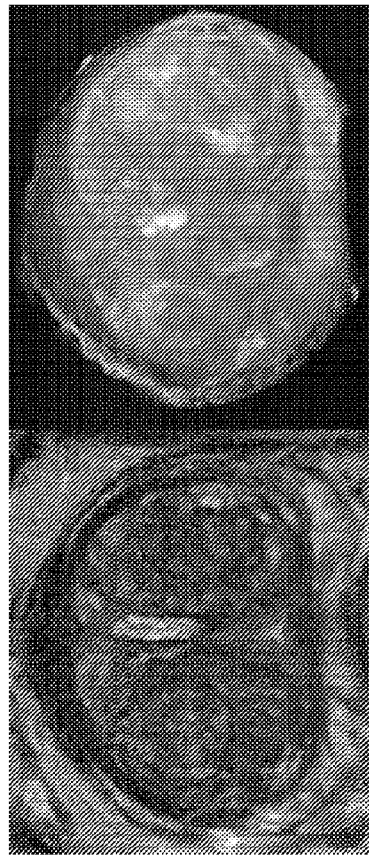
FIGS. 6A, B are illustrative views of two typical invivo and exvivo T2-weighted image slices. Between 15 ex-vivo slices, image the slice shown in FIG. 6B had the highest similarity to its corresponding in-vivo image (FIG. 6A). This shows any existing registration techniques without reslicing will fail to find best match with the highest possible similarity index between reference (invivo) and target (exvivo) images.

Referring now to FIGS. 6A, B, there is shown typical in-vivo and ex-vivo T2-weighted images. Between 15 ex-vivo slices, FIG. 6B had the highest similarity to its corresponding in-vivo image FIG. 6A. This means any existing registration techniques identified herein will fail to register these two in-vivo and ex-vivo datasets. However, using the algorithm or method of the present invention (see FIG. 1), this problem was overcome.

FIG. 7 provides pictorial views of seven typical slices from registered in-vivo and ex-vivo T2-weighted image volumes. Both in-vivo and ex-vivo image volumes were in the axial plane and there was no need to apply step 1 in FIG. 1 to transfer volumes to the desired plane, which was the axial plane. The in-vivo image volume was chosen as the reference volume. The ex-vivo image volume was chosen as the target volume. User defined control parameters were L=2 and α=10 degree. In the radial reslicing step (FIG. 5), the estimated rotation angles to register all slices of ex-vivo data with in-vivo were around ϕ=0, θ=2.5 and ψ=0 (2.5 degree in sagittal plane) for all slices because a prostate is a rigid object. In the first three register ex-vivo slices, a portion of images is vanished due to lack of data after rotation for interpolation.

FIG. 8 provides pictorial views of typical ex-vivo images: a) Original images: T2-WI and DWI (b=50,400,800 and ADC). After registering ex-vivo data with T2-WI invivo by method and steps shown in FIG. 5, an additional step was needed to be done on DWI ex-vivo data due to a severe localized geometric distortion induced by the echo planar imaging (EPI) technique. In this additional step, reference and target volumes were transferred to the coronal plane and for each slice in the coronal plane method and steps shown in FIG. 5 was used to correct distortion.

Figure 9:
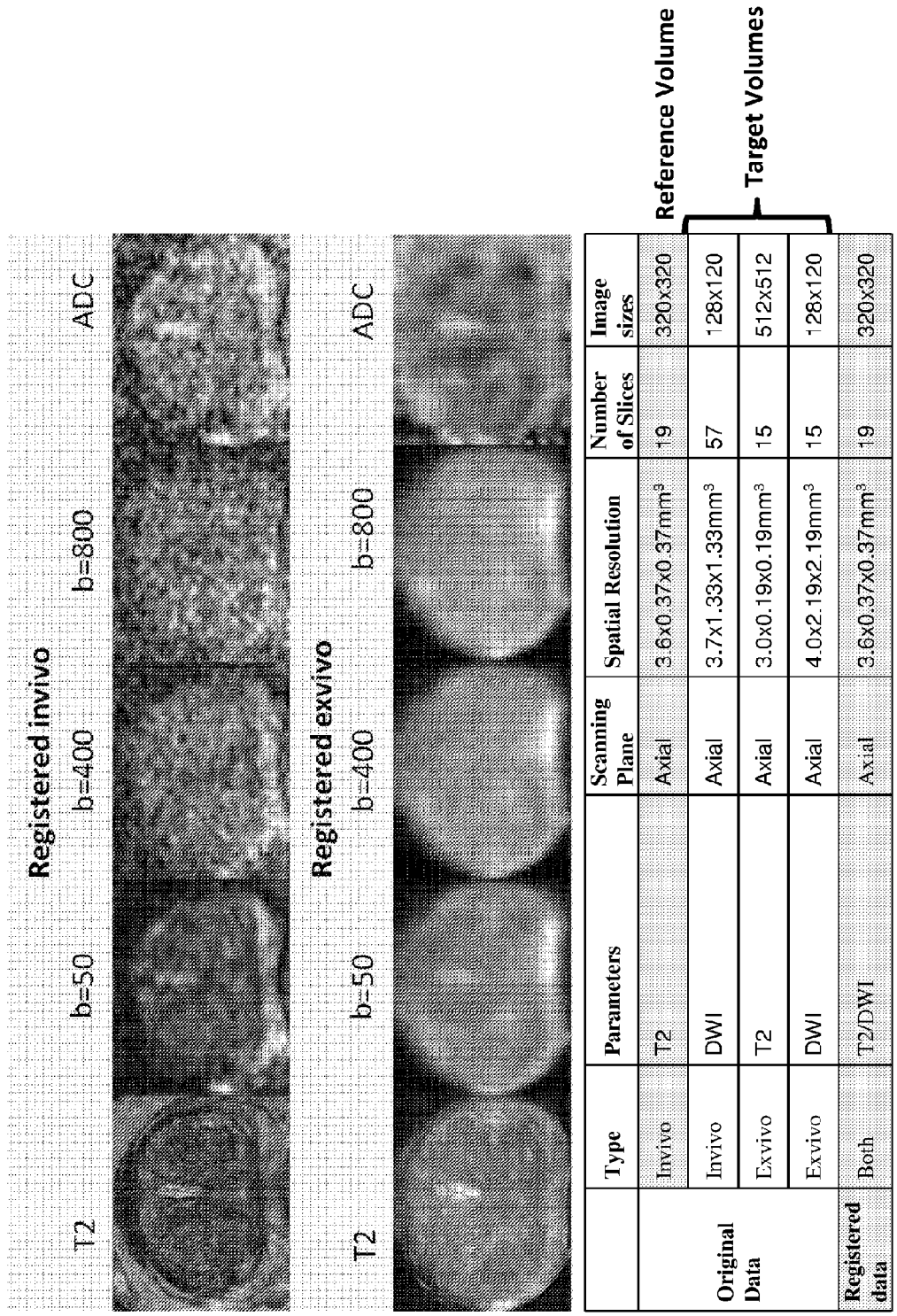
FIG. 9 provides pictorial views of registered in-vivo and ex-vivo MR parameters (T2-WI and DWI) for a typical slice.

FIG. 9 provides pictorial views of registered in-vivo and ex-vivo MR parameters (T2-WI and DWI) for a typical slice.

Registration of Whole-Body T1-Weighted Pre and Post Contrast Image Volumes

Figure 10:
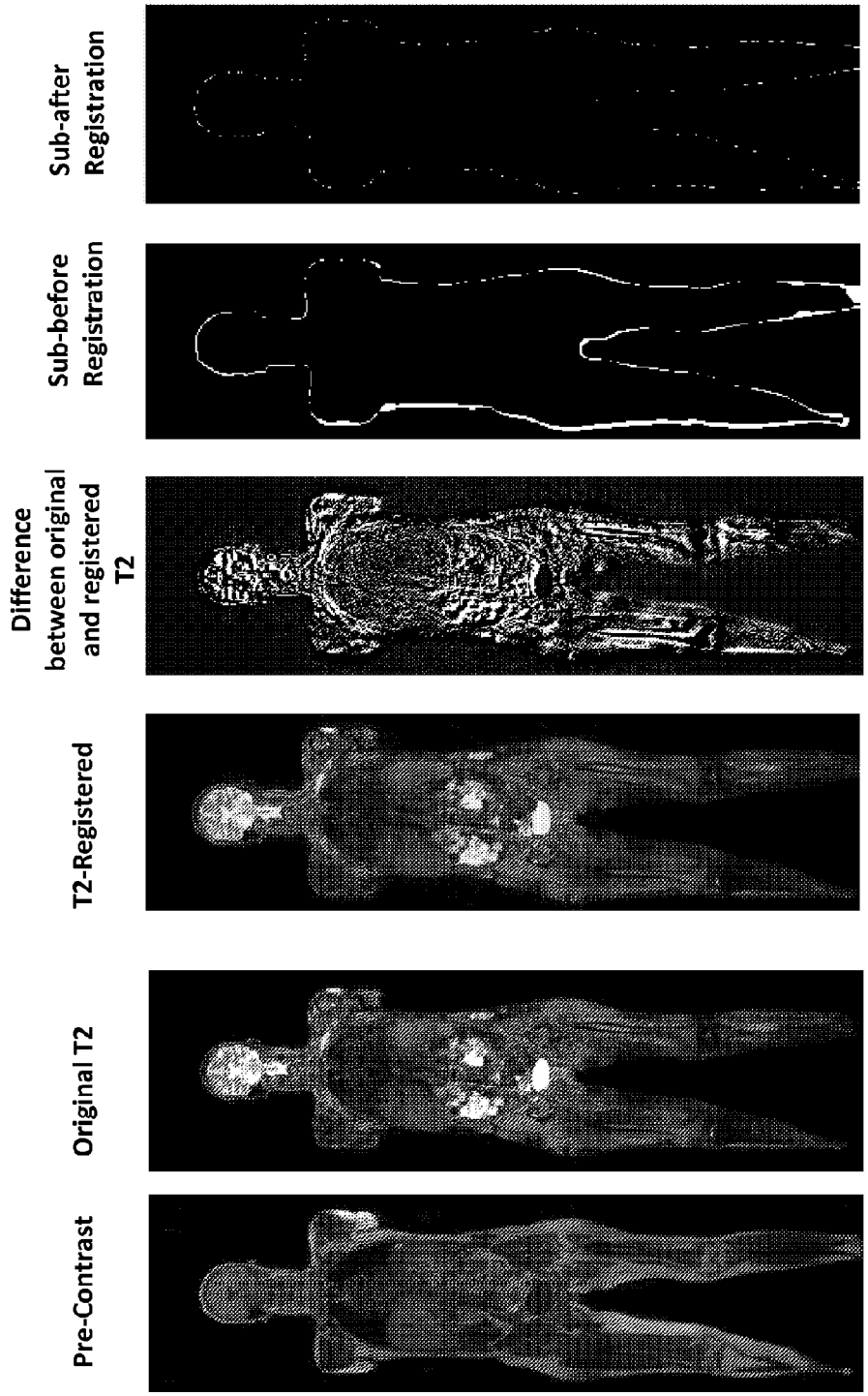
FIG. 10 provides pictorial views of registered whole-body T1-weighted pre and post contrast images. Average MSE and Dice similarity indices of slices are [0.1415 0.975] and [0.1256 0.9805], respectively before and after registration using our technology shown in FIG. 1 for co-registration of ex-vivo image volume to in-vivo image volume. Improvements in Dice similarity indices after registration using our technology respectively are 11.24% and 0.54%.
Figure 11A:
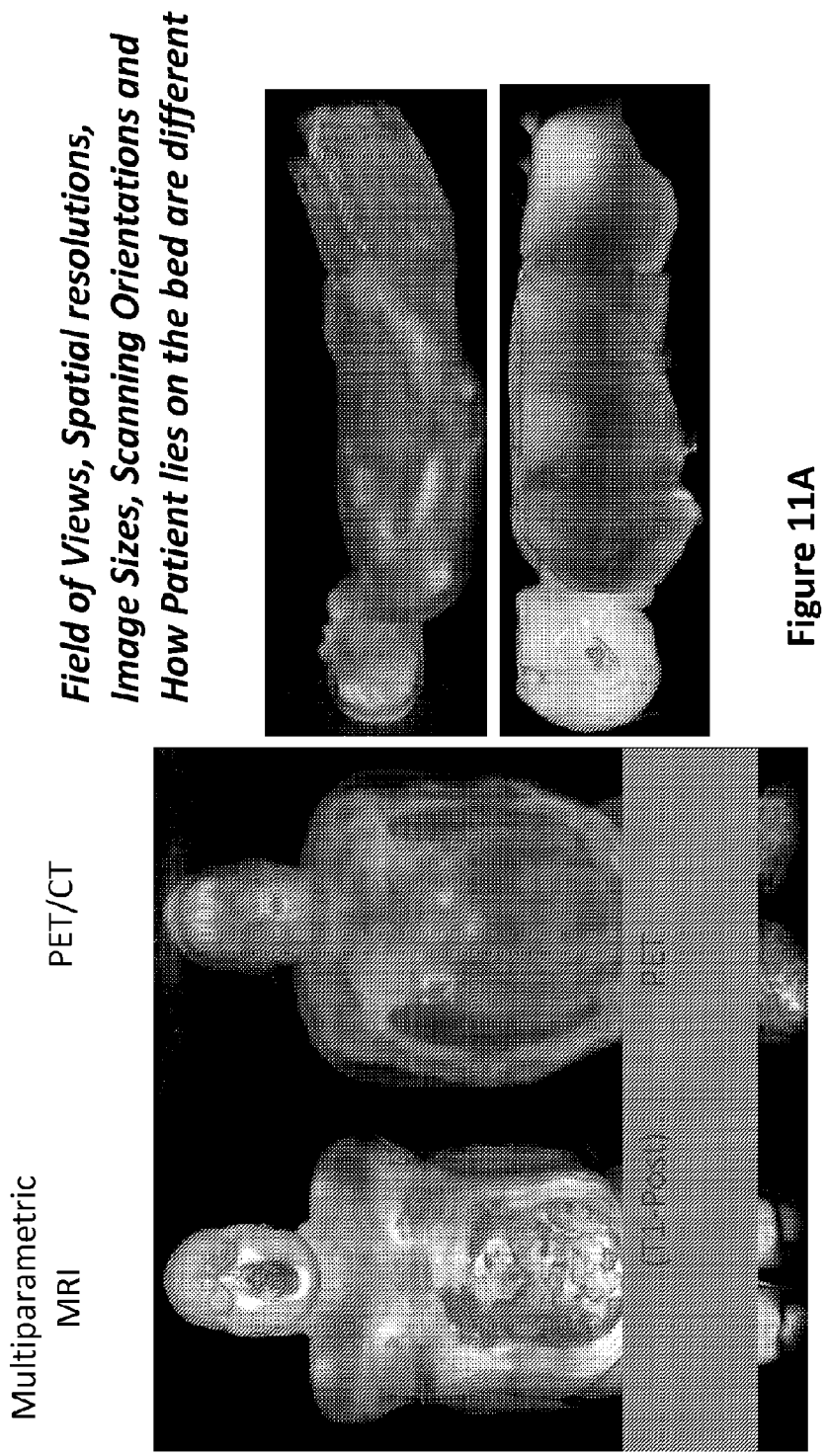
FIGS. 11A-D provide pictorial views of Multiparametric and Multimodality (MRI/PET/CT) for a typical slice, before (FIG. 11A), registration before treatment (FIG. 11B), registration after treatment (FIG. 11C), and comparison of registrations before and after treatments (FIG. 11D).
Figure 11B:
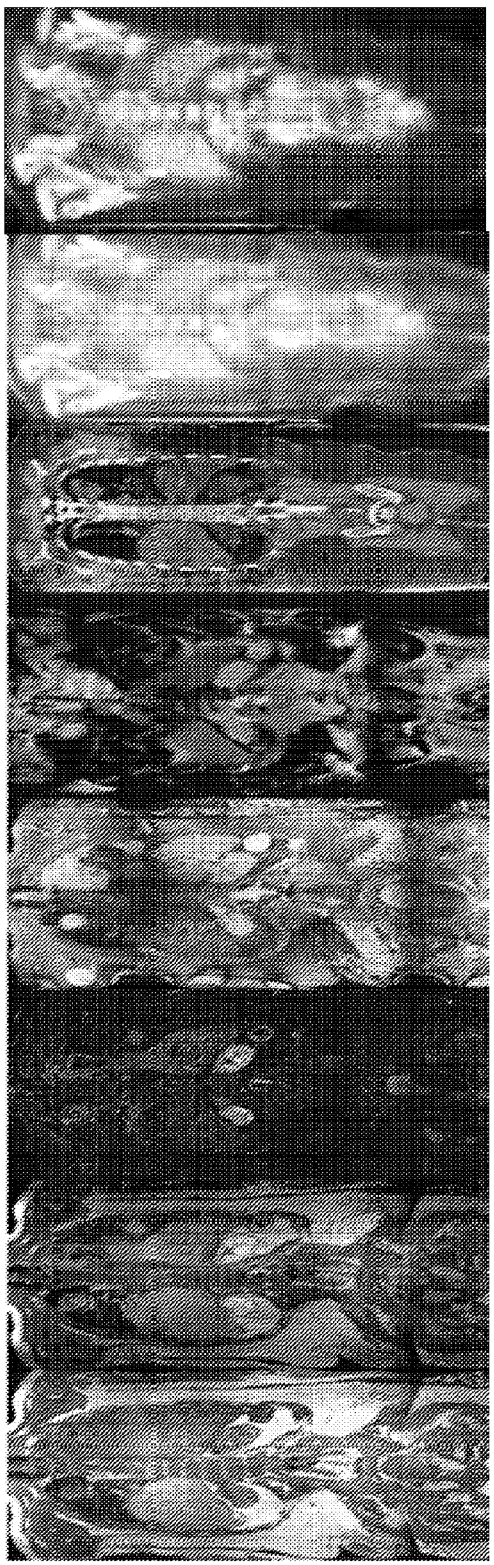
Figure 11C:
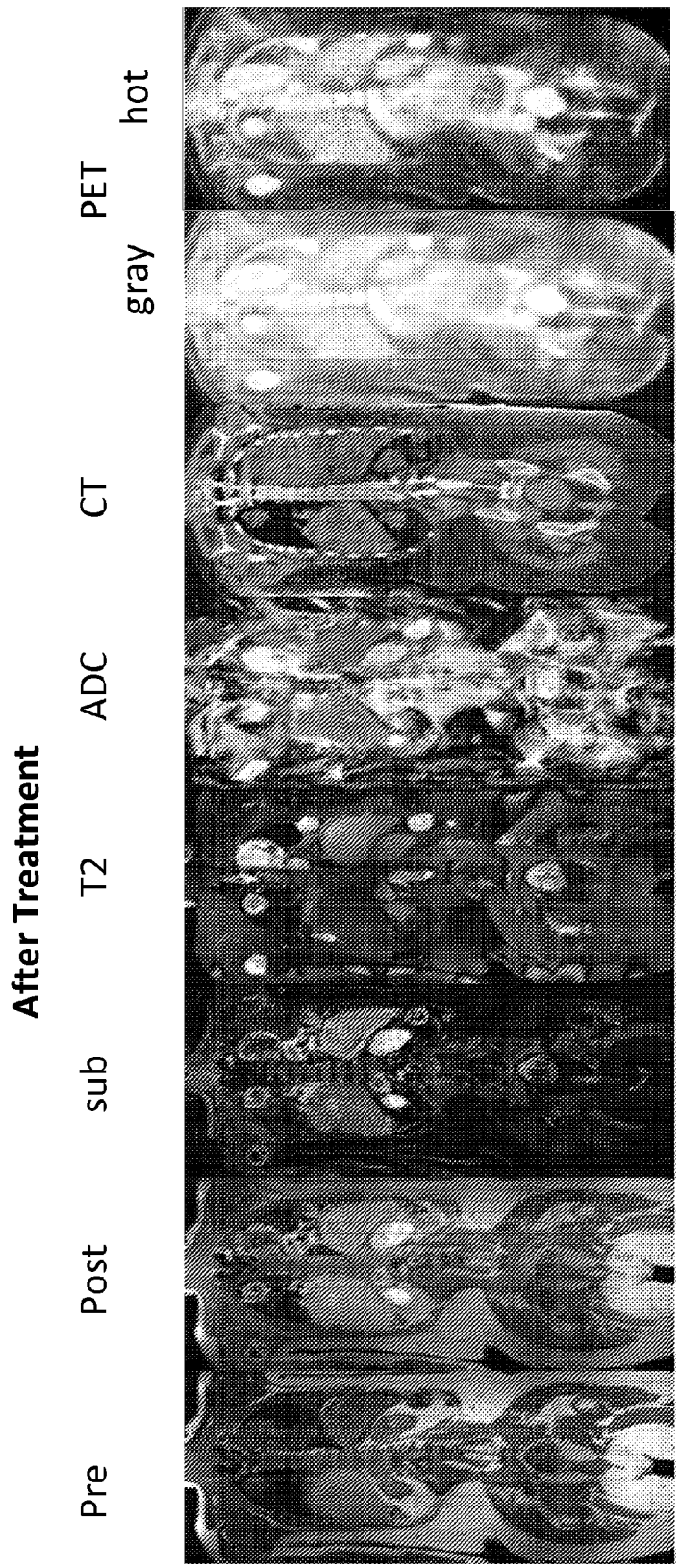
Figure 11D:
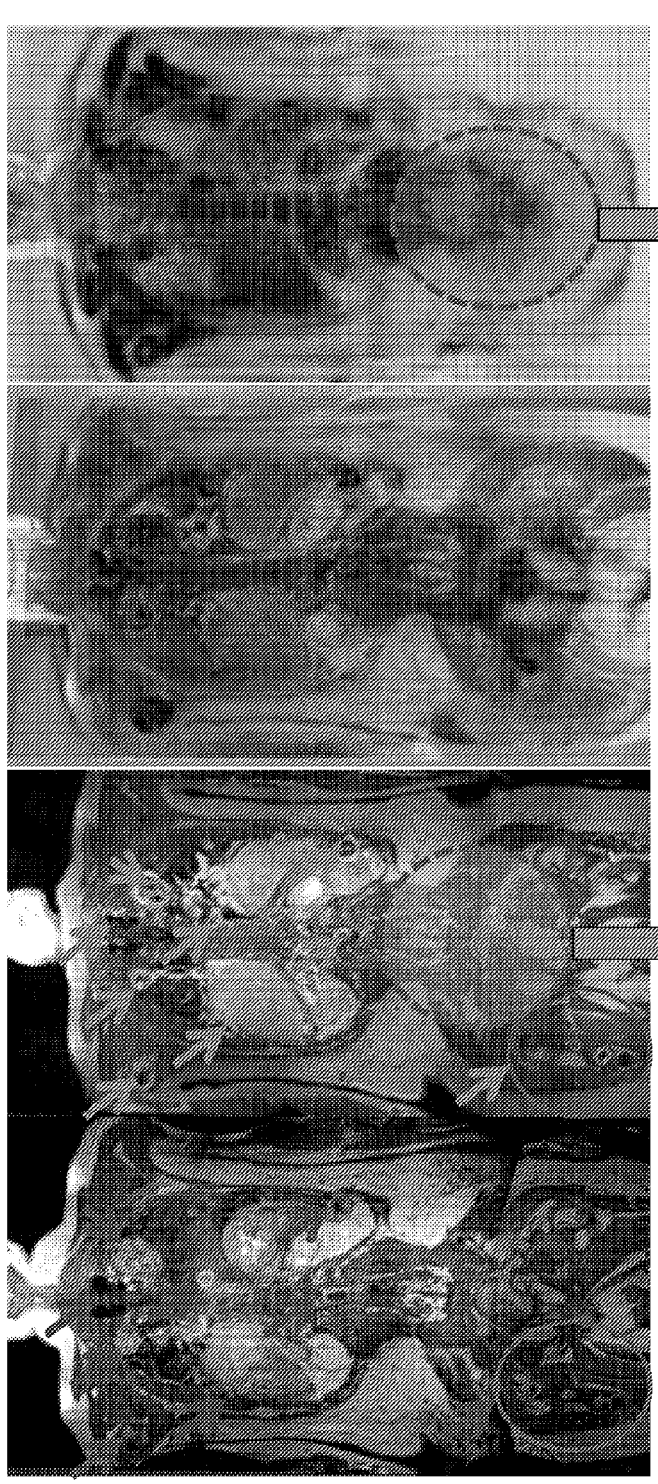

FIG. 10 provides pictorial views of registered whole-body T1-weighted pre and post contrast images for a typical slice. Average MSE and Dice similarity indices of slices are [0.1415 0.975] and [0.1256 0.9805], respectively before and after registration using the methodology shown in FIG. 1 for co-registration of ex-vivo image volume to in-vivo image volume. Improvements in Dice similarity indices after registration using the methods of the present invention technology respectively are 11.24% and 0.54%. This shows that the 3D registration presented in this invention can be also used to correct small motion artifacts Registration of Whole-body Multiparametric and Multimodality (MRI/PET/CT):

FIGS. 11A-E provide pictorial views of multiparametric and multimodality (MRI/PET/CT) for a typical slice, before (FIG. 11A), registration before treatment (FIG. 11B), registration after treatment (FIG. 11C), and comparison of registrations before and after treatments (FIG. 11D). PET/CT is less registered in circled regions in FIG. 11D, because of the patient position and 3D registration was tuned to have the best match in abdomen region, however a separate 3D registration with pelvis area as region of interest can be used to fully register circled regions as well.

Such methods of the present invention are suitable for use in combination with any of a number of computer systems as are known to those skilled in the art or hereinafter developed such as that described herein. Such a computer system includes a computer, a display, and one or more input device(s). The display is any of a number of devices known to those skilled in the art for displaying images responsive to outputs signals from the computer, including but not limited to cathode ray tubes (CRT), liquid crystal displays (LCDS), plasma screens and the like. It should be recognized that the signals being outputted from the computer can originate from any of a number of devices including PCI or AGP video boards or cards mounted with the housing of the computer that are operably coupled to the computer's microprocessor and the display. As indicated herein, such video boards or cards should be configured so as to have sufficient capacity (e.g., cache memory and processing speed) to process and display the images in near real time.

The one or more input device(s) are any of a number of devices known to those skilled in the art which can be used to provide input signals to the computer for control of applications programs and other programs such as the operating system being executed within the computer. In illustrative embodiments, the input device preferably comprises a switch, a slide, a mouse, a track ball, a glide point or a joystick or other such device (e.g., a keyboard having an integrally mounted glide point or mouse) by which a user such as student can input control signals other than by means of a keyboard.

The computer typically includes a central processing unit including one or more micro-processors such as those manufactured by Intel or AMD, Motorola or the like, random access memory (RAM), mechanisms and structures for performing I/O operations, a storage medium such as a magnetic hard disk drive(s) or other drives (fixed or removable) for storage of data, operating systems or the applications or software programs of the present invention including an applications program according to the present invention(s), and a device (not shown) for reading from and/or writing to a removable computer readable medium, such as for example an optical disk reader capable of reading CDROM, DVD or optical disks and readers of other types of nonvolatile memory such as flash drives, jump drives or spin memory that embody one or more types of non-volatile types of memory or storage devices. As indicated herein, in particular embodiments the microprocessor is preferably a multi-core type of processor having sufficient processing capability and speed as well as RAM so as to perform the method steps described herein.

Such a hard disk drive is provided for purposes of booting and storing the operating system, other applications or systems that are to be executed on the computer, paging and swapping between the hard disk and the RAM and the like. In this embodiment, an applications program according to the present invention is stored in the hard drive including the programming instructions and a data portion containing the text, auditory and visual informational data being displayed as well as the historical file of such information. Such data also can be stored in a removable computer readable medium such as a CD or DVD type of media that is inserted into a device for reading and/or writing to the removable computer readable media. Such a reading/writing device is any of a number of devices known to those skilled in the art for reading from and/or writing to the particular medium on which the applications program is stored.

In an alternative embodiment, such a computer system also includes a network based computer system that includes a server, an external storage device and a network infrastructure that operably couples a plurality or more of client computer systems to the server. The client computer systems are typically configured like the above described computer system except that in use the applications program of the present invention and related data of a condition for a given individual could be found on the server and such information would be temporarily onto the client computer system.

The server is any of a number of servers known to those skilled in the art that are intended to be operably connected to a network so as to operably link a plurality or more of client computers via the network to the server and thus also to the external storage device. Such a server typically includes a central processing unit including one or more microprocessors such as those manufactured by Intel or AMD, random access memory (RAM), mechanisms and structures for performing I/O operations, a storage medium such as a magnetic hard disk drive(s), and an operating system for execution on the central processing unit. The hard disk drive of the server typically is not used for storing data and the like utilized by client applications being executed on the client computers. Rather the hard disk drive(s) of the server are typically provided for purposes of booting and storing the operating system, other applications or systems that are to be executed on the server, paging and swapping between the hard disk and the RAM.

Data and the like being used in connection with the execution of client applications, such as the applications program of the present invention and the information and/or data related thereto, can be stored in the external storage device that is operably interconnected to the server using any of a number of techniques and related devices or cabling known to those skilled in the art. In an illustrative embodiment, such an interconnection is implemented using a small computer systems interface (SCSI) technique(s) or via a fiber optic cable or other high-speed type of interconnection.

In an illustrative, exemplary embodiment, the external storage device comprises a disk assembly typically made up of one or more hard disks that are configured and arranged so the external storage medium functionally appears to the server as a single hard disk. Such an external storage medium is further configured and arranged to implement any of a number of storage schemes such as mirroring data on a duplicate disk (RAID level 1) or providing a mechanism by which data on one disk, which disk has become lost or inaccessible, can be reconstructed from the other disks comprising the storage medium (RAID level 5). Although reference is made to a disk assembly and hard disks, this is for illustration and shall not be construed as being a limitation on the particular form of the devices or mechanism that makes up the external storage device or the medium comprising such a device.

In addition, each of the client computers includes one or more I/O ports that are operably connected to the microprocessor and which are configured and arranged for the transfer of the data and program instructions between and amongst the client computer and the server using any of a number of non-wireless techniques or wireless techniques known to those skilled in the art. Such non-wireless techniques include for example any of a number of network infrastructures known to those skilled in the art such as Ethernet, token ring, FDDI, ATM, Sonet, X.25 and Broadband.

In the case of wireless techniques, the I/O ports of the client computers are configured so as to include a transceiver as is known to those skilled in the art for wireless network transmission systems. An exemplary wireless network technique includes those systems embodying a transceiver or transmitter complying with IEEE-802.11 or other appropriate standards hereinafter developed. In each case, the transceiver operably coupled to the client computer is configured and arranged so as to establish a communications link between the client computer and a receiver or transceiver remote from the location of the client computer that is in turn operably coupled to the server. The server in turn could be coupled to the remotely located transceiver/receiver using non-wireless or wireless techniques.

Although a preferred embodiment of the invention has been described using specific terms, such description is for illustrative purposes only, and it is to be understood that changes and variations may be made without departing from the spirit or scope of the following claims.

Incorporation by Reference

All patents, published patent applications and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method for registration of multiparametric and modality images or objects, comprising the steps of:
acquiring image data in slices;
processing the acquired image data; and
wherein said processing comprises
resizing number of slices in one of a plurality of planes or all planes to a desired size using orthogonal reslicing and to obtain resampled target volume (RTV), registration parameters estimation based on non-uniform radial reslicing: searching for best match between reference slices and resampled target volume (RTV) slices, and non-uniform radial reslicing comprising (i) 3D rotation, (ii) slice-by-slice affine transformation (translation and scale only) of the resampled target volume (RTV), and (iii) search which slices of RTV, after applying (i) and (ii), are similar to slices of the reference volume.

2. The registration method of claim 1, wherein the 3D rotation angles is defined by the relationship ($\phi$, $\theta$ and $\psi$), where $\phi$, $\theta$ and $\psi$ can be between −90 and 90 degree.

3. The registration method of claim 1, wherein the reslicing plane is one of axial, coronal and/or sagittal.

4. The registration method of claim 1, wherein said non-uniform radial resampling includes 3D affine transforms ($A=\{a_i\}_{i=1:NR}$) to select some of slices of resampled target volume (RTV), obtained by 3D resampling of the target volume to a spatial resolution higher than spatial resolution of the reference volume, in a non-uniform manner, such a 3D affine transform includes parameters of 3D rotations, translation and scaling estimated using an optimization search routine.

5. The registration method of claim 1, wherein said processing of the acquired data includes correcting for at least one of field of view, slice thickness and orientation.

6. The registration method of claim 1, wherein said imaging technique is one of a MRI, CT, X-ray, PET and UT imaging technique.

7. The registration method of claim 1, wherein said acquiring image data includes acquiring image data of a given region of interest using one imaging technique and acquiring image data for said given region of interest using a second imaging technique and wherein said processing includes processing the acquired image data from both imaging techniques so that the image data of said one technique is co-registered with the acquired data using said second imaging technique.

8. The registration method of claim 7, wherein said one imaging technique is one of a MRI, CT, X-ray, PET and UT imaging technique and wherein said second imaging technique is the other of an MRI, CT, X-ray, PET and UT imaging technique.

9. The registration method of claim 1, said acquiring image data includes acquiring one image data of a given region of interest using one imaging technique and acquiring another image data for said given region of interest using said one imaging technique; wherein said processing includes processing the acquired image data for said one and said another imaging data, and wherein said imaging technique is one of a MRI, CT, X-ray, PET and UT imaging technique.

10. A system for registration of multiparametric and modality images or objects, comprising:
one of a microprocessor, digital signal processor or ASIC; and
a software program for execution on said one of the microprocessor, digital signal processor or ASIC, said software comprising program comprising code elements, criteria and instructions in a form that instructs said one of the microprocessor, digital signal processor or ASIC to perform functions of:
processing acquired image data wherein said processing comprises:
resizing number of slices in one of a plurality of planes or all planes to a desired size using orthogonal reslicing and to obtain resampled target volume (RTV),
registration parameters estimation based on non-uniform radial reslicing: searching for best match between reference slices and resampled target volume (RTV) slices, and
non-uniform radial reslicing comprising (i) 3D rotation, (ii) slice-by-slice affine transformation (translation and scale only) of the resampled target volume (RTV), and (iii) search which slices of RTV, after applying (i) and (ii), are similar to slices of the reference volume.

11. The registration method of claim 10, wherein the 3D rotation angles is defined by the relationship ($\phi$, $\theta$ and $\psi$), where $\phi$, $\theta$ and $\psi$ can be between −90 and 90 degree.

12. The registration method of claim 10, wherein the reslicing plane is one of axial, coronal and/or sagittal.

13. The registration method of claim 10, wherein said non-uniform radial resampling includes 3D affine transforms ($A=\{a_i\}_{i=1:NR}$) to select some of slices of resampled target volume (RTV), obtained by 3D resampling of the target volume to a spatial resolution higher than spatial resolution of the reference volume, in a non-uniform manner, such a 3D affine transform including parameters of 3D rotations, translation and scaling estimated using an optimization search routine.

14. The registration system of claim 10, wherein said processing of the acquired data includes correcting for at least one of field of view, slice thickness and orientation.

15. The registration system of claim 10, wherein said imaging technique is one of a MRI, CT, X-ray, PET and UT imaging technique.

16. The registration system of claim 10, wherein the acquired image data comprises image data of a given region of interest using one imaging technique and image data for said given region of interest using a second imaging technique and wherein said processing includes processing the acquired image data from both imaging techniques so that the image data of said one technique is co-registered with the acquired data using said second imaging technique.

17. The registration system of claim 10, wherein said one imaging technique is one of a MRI, CT, X-ray, PET and UT imaging technique and wherein said second imaging technique is the other of an MRI, CT, X-ray, PET and UT imaging technique.

18. The registration system of claim 10, wherein the acquired image data includes one set of image data of a given region of interest using one imaging technique and another set of image data for said given region of interest using said one imaging technique; wherein said processing includes processing the acquired image data for said one and said another imaging data, and wherein said imaging technique is one of a MRI, CT, X-ray, PET and UT imaging technique.

* * * * *